(12) United States Patent
Cohn et al.

(10) Patent No.: US 11,376,131 B2
(45) Date of Patent: Jul. 5, 2022

(54) CORTICAL RIM-SUPPORTING INTERBODY DEVICE AND METHOD

(71) Applicant: Ethicon, Inc., Somerville, NJ (US)

(72) Inventors: William Cohn, Houston, TX (US); Terry Daglow, Houston, TX (US); Megan Greenwood, Houston, TX (US); Joseph Labdik, Houston, TX (US); Roman Lomeli, Raynham, MA (US); Ravi Patel, Raynham, MA (US); Byron Smith, Memphis, TN (US); Fergus Wong, Houston, TX (US)

(73) Assignee: Ethicon, Inc., Somerville, NJ (US)

( * ) Notice: Subject to any disclaimer, the term of this patent is extended or adjusted under 35 U.S.C. 154(b) by 105 days.

(21) Appl. No.: 16/841,721

(22) Filed: Apr. 7, 2020

(65) Prior Publication Data

US 2021/0307928 A1    Oct. 7, 2021

(51) Int. Cl.
| | | |
|---|---|---|
| *A61F 2/44* | (2006.01) | |
| *A61F 2/46* | (2006.01) | |
| *A61B 17/88* | (2006.01) | |
| *A61B 17/02* | (2006.01) | |
| *A61F 2/30* | (2006.01) | |

(52) U.S. Cl.
CPC ........ *A61F 2/4455* (2013.01); *A61B 17/8811* (2013.01); *A61B 17/8855* (2013.01); *A61F 2/441* (2013.01); *A61F 2/442* (2013.01); *A61F 2/4611* (2013.01); *A61B 2017/0256* (2013.01); *A61F 2002/3008* (2013.01); *A61F 2002/30092* (2013.01); *A61F 2002/30583* (2013.01)

(58) Field of Classification Search
CPC ............ A61B 17/8852; A61B 17/8855; A61B 17/8858; A61F 2/44; A61F 2/441; A61F 2/442; A61F 2002/4435
See application file for complete search history.

(56) References Cited

U.S. PATENT DOCUMENTS

| | | | | |
|---|---|---|---|---|
| 5,888,220 A | * | 3/1999 | Felt | A61F 2/4611 |
| | | | | 128/898 |
| 6,248,131 B1 | * | 6/2001 | Felt | A61B 17/1739 |
| | | | | 606/247 |
| 6,332,894 B1 | * | 12/2001 | Stalcup | A61F 2/4465 |
| | | | | 623/17.11 |
| 8,007,535 B2 | | 8/2011 | Hudgins | |
| 9,592,130 B2 | * | 3/2017 | Hibri | A61F 2/441 |
| 10,758,288 B2 | * | 9/2020 | Lomeli | A61F 2/4611 |
| 10,806,593 B2 | * | 10/2020 | Lomeli | A61F 2/442 |
| 2003/0028251 A1 | * | 2/2003 | Mathews | A61M 25/10 |
| | | | | 623/17.16 |
| 2003/0220695 A1 | * | 11/2003 | Sevrain | A61F 2/442 |
| | | | | 623/17.16 |

(Continued)

*Primary Examiner* — Eric S Gibson

(57) ABSTRACT

An inflatable central distractor is inserted in to a disc space between two vertebral endplates. A perimeter balloon is inserted into the disc space in such a manner as to surround the central inflatable distractor. The perimeter balloon and the central inflatable distractor are simultaneously expanded such that as the central inflatable distractor expands the perimeter balloon surrounds the central inflatable distractor and such that the central inflatable distractor and the perimeter balloon, when expanded, contribute to forcing adjacent vertebral endplates apart.

6 Claims, 27 Drawing Sheets

(56) References Cited

U.S. PATENT DOCUMENTS

| | | | | |
|---|---|---|---|---|
| 2004/0230309 | A1* | 11/2004 | DiMauro | A61F 2/4425 |
| | | | | 623/17.12 |
| 2005/0090901 | A1* | 4/2005 | Studer | A61F 2/441 |
| | | | | 623/17.12 |
| 2005/0119752 | A1* | 6/2005 | Williams | A61F 2/442 |
| | | | | 623/17.16 |
| 2007/0255406 | A1* | 11/2007 | Trieu | A61F 2/4611 |
| | | | | 623/17.11 |
| 2009/0112323 | A1* | 4/2009 | Hestad | A61F 2/4611 |
| | | | | 623/17.12 |
| 2009/0222093 | A1* | 9/2009 | Liu | A61F 2/442 |
| | | | | 623/17.12 |
| 2010/0256766 | A1* | 10/2010 | Hibri | A61F 2/442 |
| | | | | 623/17.16 |
| 2011/0137317 | A1* | 6/2011 | O'Halloran | A61B 17/8855 |
| | | | | 606/92 |
| 2014/0100581 | A1* | 4/2014 | Reimels | A61B 17/8858 |
| | | | | 606/99 |
| 2014/0277465 | A1* | 9/2014 | Teisen | A61F 2/4611 |
| | | | | 623/17.12 |
| 2014/0378980 | A1* | 12/2014 | Lomeli | A61F 2/4611 |
| | | | | 606/90 |
| 2017/0340454 | A1* | 11/2017 | Lomeli | A61B 17/3421 |
| 2018/0271576 | A1* | 9/2018 | Lomeli | A61B 17/7097 |
| 2020/0352616 | A1* | 11/2020 | Lomeli | A61F 2/442 |
| 2021/0307928 | A1* | 10/2021 | Cohn | A61F 2/4611 |

\* cited by examiner

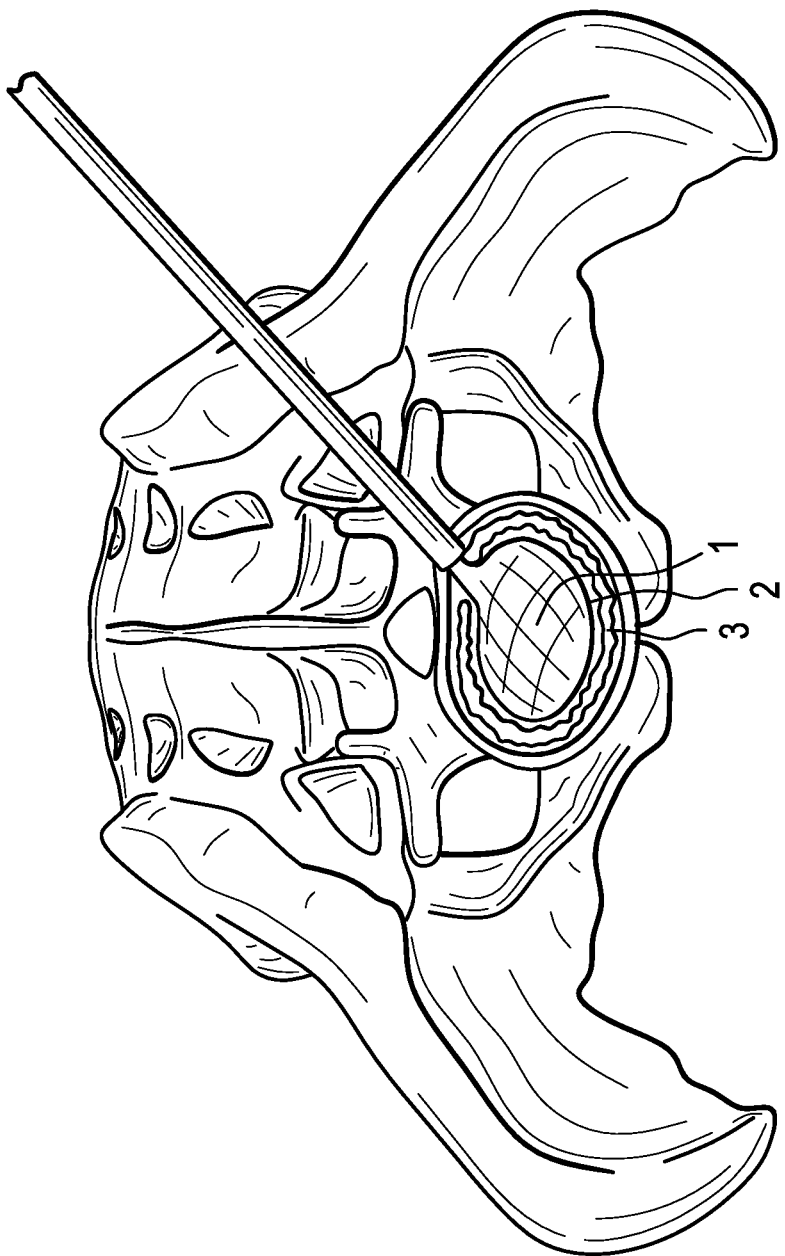

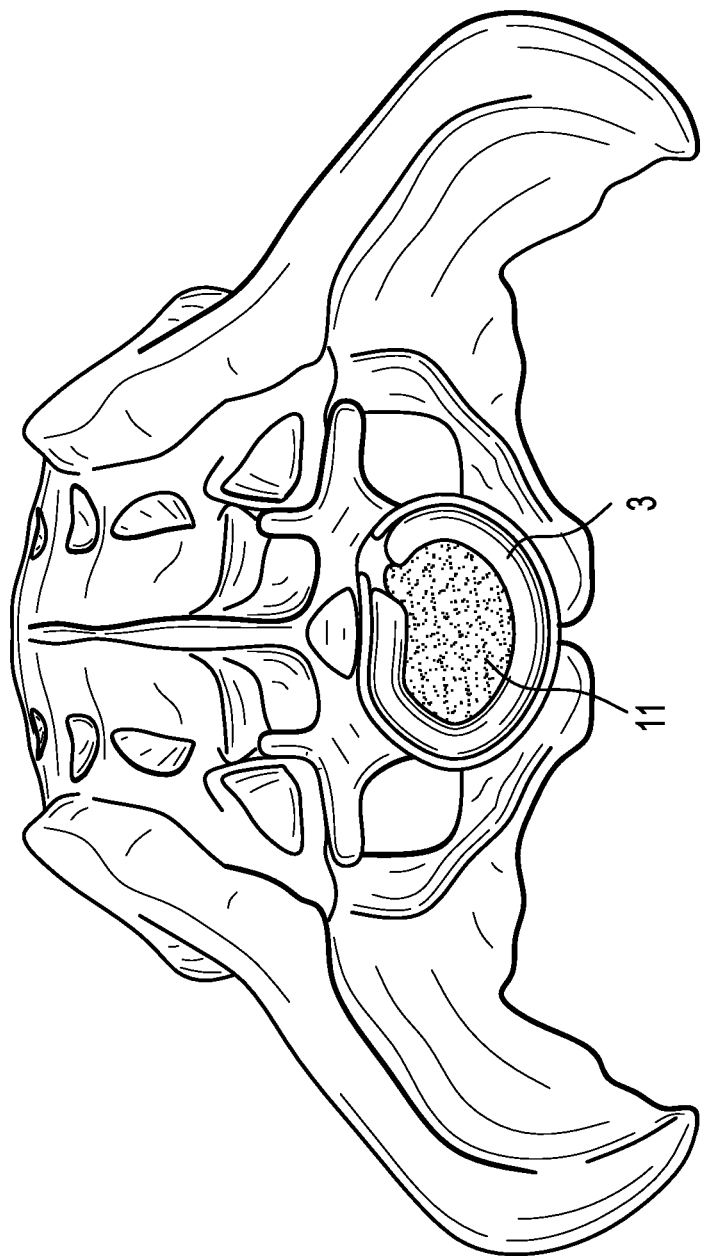

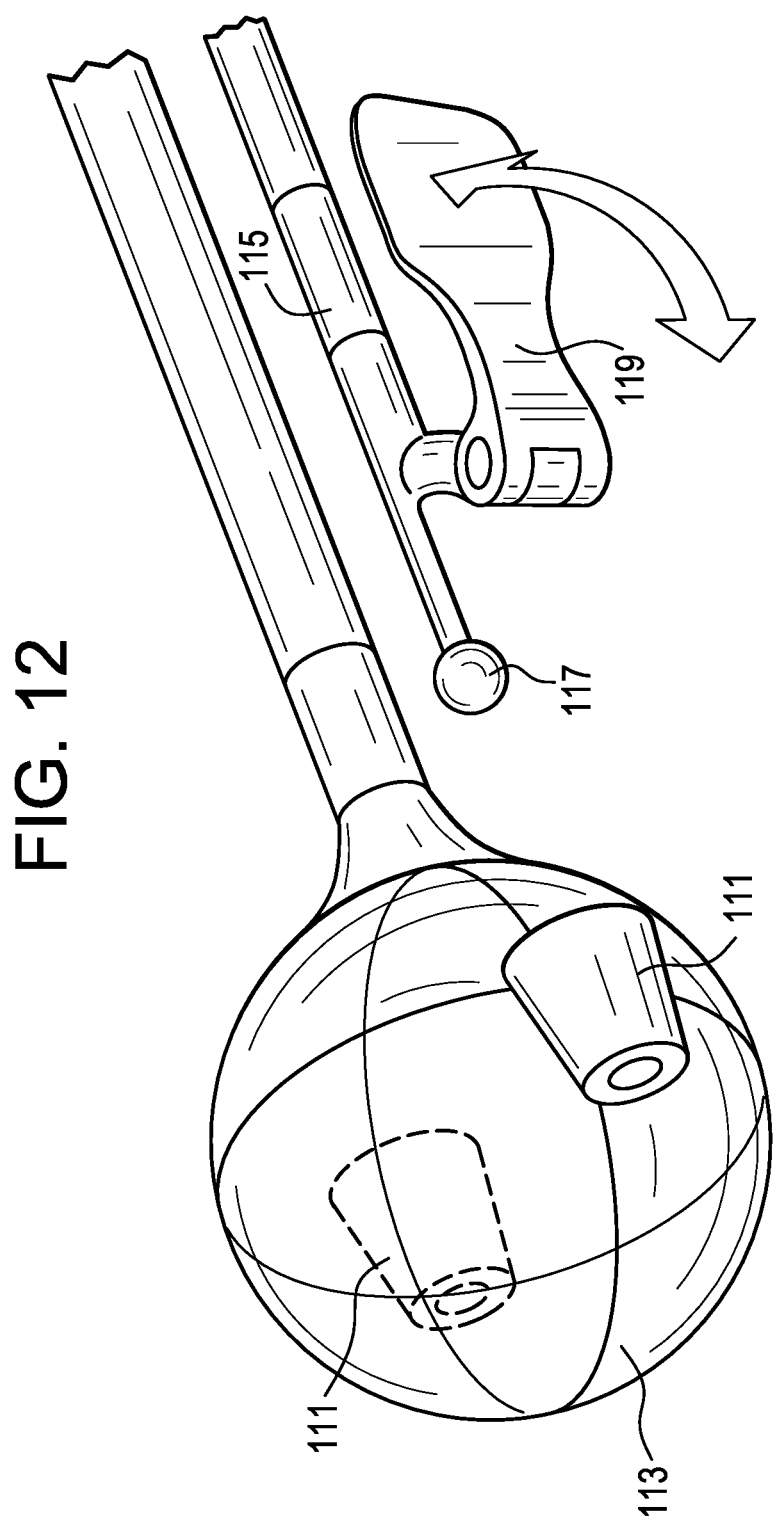

CORTICAL RIM-SUPPORTING INTERBODY DEVICE AND METHOD

BACKGROUND OF THE INVENTION

Field of the Invention

In an effort to treat low back pain, surgeons remove the degenerative disc and insert a fusion cage into the disc space. In an effort to minimize the invasiveness of the fusion procedure, more recent efforts have focused on forming the fusion cage in-situ by flowing a curable material into a balloon that has been placed into the disc space.

Subsidence of an implanted interbody cage is a known risk in fusion and there is a higher occurrence for patients with lower bone density. Hou and Yuan, Spine Journal, 12, 3, 249-256 (2012) investigated the structural properties of lumbar endplates and reported that the periphery of the endplates particularly in the posterolateral region near the pedicles were significantly stronger than the central region. They also concluded that with increasing disc degeneration, the central region became weaker while minimal strength changes were observed in the peripheral region.

Discussion of the Related Art

US Patent Publication 2004/0230309 (DePuy Spine) discloses an orthopedic device for implanting between adjacent vertebrae comprising: an arcuate balloon and a hardenable material within said balloon. In some embodiments, the balloon has a footprint that substantially corresponds to a perimeter of a vertebral endplate. An inflatable device is inserted through a cannula into an intervertebral space and oriented so that, upon expansion, a natural angle between vertebrae will be at least partially restored. At least one component selected from the group consisting of a load-bearing component and an osteobiologic component is directed into the inflatable device through a fluid communication means.

U.S. Pat. No. 8,007,535 (Hudgins) discloses an injectable annular ring useful in treating a deteriorating spinal disc. When used, the annular ring may be collapsed or folded in order for it to be placed through a small opening in a prepared intervertebral space within the annulus using minimally invasive techniques. Deployment or unfolding the ring in the intervertebral space provides an interior cavity bordered by the ring that is in direct contact with the vertebral endplates. When an internal volume of the ring is injected or filled with a load-bearing, hardenable material, the filled ring maintains the intervertebral spacing and prevents the rings from being expelled from the interior cavity through the small annular opening.

U.S. Pat. No. 6,332,894 (Stalcup) discloses an orthopedic implant for implanting between adjacent vertebrae and a spine, includes a generally annular bag; and hardened polymer within the bag. The method of fusing adjacent vertebrae in a spine includes the steps of forming an access hole in an annulus of a disc between the adjacent vertebrae; removing the nucleus within the disc to form a cavity surrounded by the annulus; placing a generally annular bag within the cavity filling the bag with a polymer; injecting bone particles into the cavity surrounded by the annular bag; and hardening the polymer.

US Published Patent Application 2003/0028251 (Mathews) discloses methods and instruments for preparing a disc space and for forming interbody devices therein. The instruments include distractors having enlargeable portions positionable in the disc space for distracting the disc space. The enlargeable portions can also provide form about or against which an interbody device of a first material is placed. A second material may be placed in the disc space previously occupied by the distractors.

US Published Patent Application 2005/0119752 (Williams) discloses devices and methods for manufacturing devices for treating degenerated and/or traumatized intervertebral discs. Artificial discs and components of discs may include an artificial nucleus and/or an artificial annulus and may be comprised of shape memory materials synthesized to achieve desired mechanical and physical properties. An artificial nucleus and/or annulus according to the invention may comprise one or more hollow bodies that may be filled with a curable material for deployment. A hollow body according to the invention may comprise one or more partitions to define one or more chambers and may comprise means for directing the flow of material within said hollow body. FIG. 19a of Williams discloses a two-balloon design comprising a central balloon and a perimeter balloon.

SUMMARY OF THE INVENTION

In accordance with an embodiment of the present invention, a method of forming an interbody fusion cage is disclosed. A central distractor is inserted into a disc space between vertebral endplates. A perimeter balloon is inserted into the disc space such that the perimeter balloon is wrapped around the central inflatable distractor. The central distractor and the perimeter balloon are expanded such that as the central inflatable distractor expands, the perimeter balloon surrounds the central inflatable distractor and such that the central distractor and the perimeter balloon, when expanded, contribute to forcing adjacent vertebral endplates apart.

In accordance with another embodiment of the invention, a method of introducing an interbody fusion cage to a disc space is disclosed. In this method, a deflated central distractor which is coupled to first and second guidewires is inserted into a disc space between vertebral endplates. A first perimeter balloon having a guidewire lumen extending through an inner diameter is slid along the guidewire into the disc space such that the first perimeter balloon is adjacent the central distractor. A second perimeter balloon having guidewire lumen extending through an inner diameter is slid along the guidewire into the disc space such that the second perimeter balloon is adjacent the central distractor.

In a further embodiment, a method of forming an interbody fusion cage is disclosed. A central distractor is inserted into a disc space between vertebral endplates via a first lumen. A distal end of the first lumen is guided into the disc space while a proximal end extends external to a patient's body. A perimeter balloon is inserted into the disc space via a second lumen which has a proximal and a distal end. The distal end of the second lumen is guided into the disc space while the proximal end of the second lumen extends from the patient's body. The proximal end of the first lumen is coupled to the proximal end of the second lumen. The perimeter balloon and the central distractor are expanded by filling the perimeter balloon with a curable material and filling the central distractor with a biologically inert fluid. Once the curable material has cured, the first and second lumens are uncoupled and the central distractor is retracted from the disc space leaving a central void.

In still a further embodiment, an apparatus for forming an intervertebral fusion device is disclosed. A central distraction device is attached to first and second guidewires. A first perimeter balloon assembly including a perimeter balloon having concentric guidewire and inflation lumens is provided. The guidewire lumen extends through an inner diameter of the first perimeter balloon and the inflation lumen extends from the first perimeter balloon to an external inflation point. A second perimeter balloon assembly including a perimeter balloon having concentric guidewire and inflation lumens is provided. The guidewire lumen extends through an inner diameter of the second perimeter balloon and the inflation lumen extending from the second perimeter balloon to an external inflation point. The first guidewire extends through the guidewire lumen of the first perimeter balloon and the second guidewire extends through the guidewire lumen of the second perimeter balloon.

In another embodiment a novel intervertebral fusion device is provided. An external balloon is configured to fill an intervertebral space when inflated. A first lumen is connected to the external balloon. An internal balloon is enclosed within the exterior balloon, the internal balloon being smaller than the external balloon. A second lumen is disposed within the first lumen and connected to the internal balloon. The internal balloon is configured such that when inflated a horseshoe or toroidal shape is formed between the internal balloon and the external balloon.

In still another embodiment, an intervertebral fusion device is provided that is configured for insertion into a disc space between vertebral endplates. An inflatable perimeter balloon is operatively associated with means for filling the inflatable perimeter balloon with a curable material such that the inflatable perimeter balloon defines a substantially toroidal shape having an open cavity. A central distractor is disposed in the open cavity and is operatively associated with means for expanding the central distractor such that a distraction force is provided against the vertebral endplates by the inflatable perimeter balloon and the biological fluid in the cavity.

In a further embodiment, a method for forming an intervertebral fusion device is provided. At least one inflatable balloon is introduced into a disc space in an uninflated state. The inflatable balloon is filled through at least one fluid communication device with a curable material such that the balloon defines a substantially toroidal shape having an open cavity substantially in a center of a vertebral endplate. The cavity is simultaneously filled with a biologically inert fluid, such that at least a portion of overall distraction force is provided by both the balloon and the fluid in the cavity and such that the distraction force is dispersed across a large majority of the vertebral endplate area throughout the range of distraction. The fluid is then removed from the cavity after the curable material in the balloon has cured. The cavity is then filled with an osteogenic material.

In yet a further embodiment, a method for forming an intervertebral fusion device is provided. A balloon assembly comprising an inner balloon disposed within an outer balloon is introduced into a disc space where the inner and outer balloons are in an uninflated state. The outer balloon is filled through at least one fluid communication means with a curable material such that an outer surface of the outer balloon contacts upper and lower vertebral endplates. The inner balloon is filled such that an outer surface of the inner balloon contacts an inner surface of the outer balloon only in the areas where the outer surface of the outer balloon contacts the upper endplate and the lower endplate, thereby forming a substantially toroidal shape in the volume containing the curable material.

BRIEF DESCRIPTION OF THE DRAWINGS

FIGS. 1A-L shows the step-wise process for making an in-situ formed device.

FIG. 12 shows an inflated balloon having a docking port for docking an instrument.

DETAILED DESCRIPTION OF THE PREFERRED EMBODIMENTS

The present invention relates to intervertebral fusion devices and methods and devices of forming and delivering intervertebral fusion devices. In embodiments of the invention, an expandable central distractor is at least partially bounded by an expandable perimeter distractor. The expandable central and perimeter distractors are simultaneously expanded so as to be positioned within a disc space to each bear a portion of the distraction load. As used herein, simultaneous expansion encompasses expanding the central and perimeter distractors coincidentally at either the same or different rates of expansion as well as expanding the central and perimeter distractors in stepwise fashion.

Figure 1A:
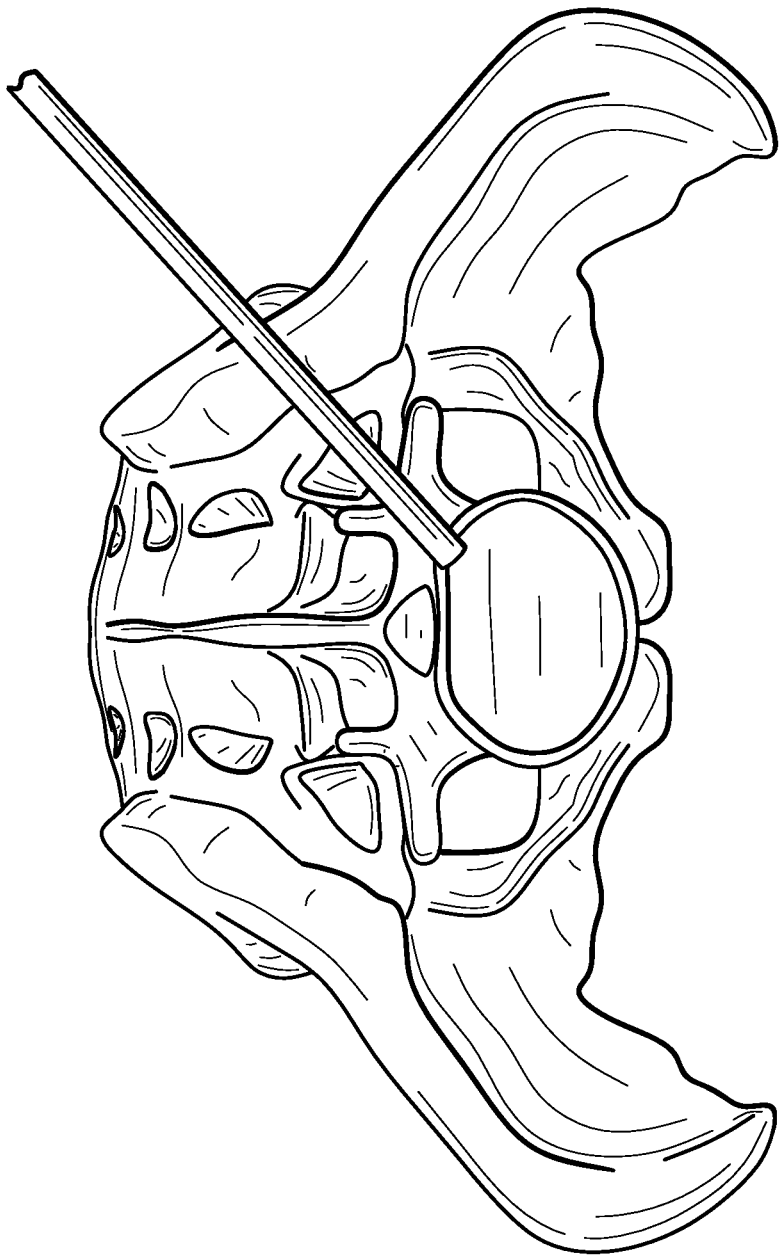

In accordance with a method embodiment of the invention, in a first step, and now referring to FIG. 1A, the surgeon removes at least the nucleus pulposus portion of the disc targeted for removal.

Figure 1B:
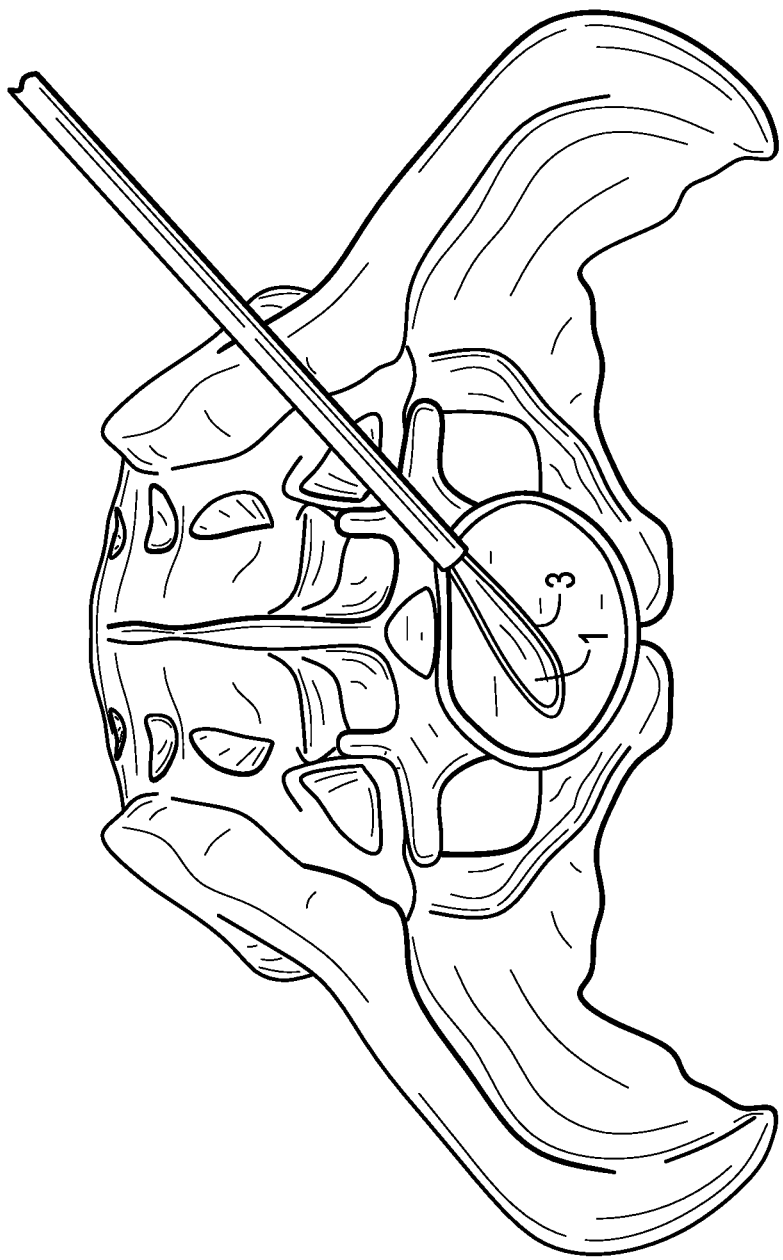

In a second step, and now referring to FIG. 1B, a central inflatable distractor and a perimeter balloon are inserted into a disc space and positioned in a central region thereof.

Typically, in this position, the perimeter balloon is wrapped around the central inflatable distractor so that the inner surface of the perimeter balloon contacts the outer perimeter of the inflated distractor. As used herein, balloon refers to a pressure vessel with at least one fluid communication means for pressurizing, by inflating it with a fluid or gas or packing it with discrete solid masses, capable of existing in a collapsed configuration (negligible/small enclosed volume) or an expanded configuration (significant enclosed volume) when pressurized. The material of the balloon may be made out of any of a wide variety of polymers, woven or nonwoven fibers, fabrics, metals such as stainless steel, titanium, or nitinol, metal mesh, and carbon.

In some embodiments, balloons may be introduced individually into the disc space, a central balloon first which is then partially inflated to anchor it in the notch created by the concave vertebral endplate surfaces above and below. Thereafter, at least one perimeter balloon is introduced using at least one guidewire attached to the central balloon. The guidewire is used to position each balloon accurately. In other embodiments, the central and perimeter balloons are locked together to maintain position relative to one another. In still other embodiments, the inter-disc position of the balloons is locked in place via a locking system external to the body.

In a third step, and now referring to FIG. 1C, the central inflatable distractor is inflated and thereby separates the vertebral endplates to a designated height as disclosed in U.S. Patent Application Publication No. 20180271576. In some embodiments, central and perimeter balloons will share the distraction load by being inflated simultaneously, i.e., either at the same time or in stepwise pressure intervals. The central and perimeter balloons provide lift force on a large majority of the endplates, meaning more than 50% of the available endplate area, preferably 100% of the available area (not including the intact annulus fibrosis). This has the added benefits of: i) maximizing the endplate lift surface and therefore minimizing the lift pressure acting on the endplate; ii) locating a portion of the lifting force onto the strongest part of the bone (cortical rim); and iii) allowing for larger lift forces in patients with more resistance to vertebral distraction In some embodiments, the perimeter balloon may be inflated to low pressure first to remove twists or pinch points that may become impinged when the central balloon is inflated, thereby simplifying the insertion process by reducing the need for precise orientation and position of the devices.

In still other embodiments, an inflation controller may be used to enable efficient lift by leveraging creep deformation while also removing the risk of endplate fracture caused by inflating the balloon too quickly. The inflation controller may be comprised of a motor-driven syringe pump and inline pressure sensor that is coupled to the perimeter and central balloons. Pressure readouts are used as inputs to control injection volume thereby maintaining constant pressure and force within the disc space. It is known that spinal tissues exhibit the characteristic of creep, such that when they are exposed to a constant tensile stress they will elongate. Therefore, exerting a constant force will distend the interbody space.

Figure 1D:
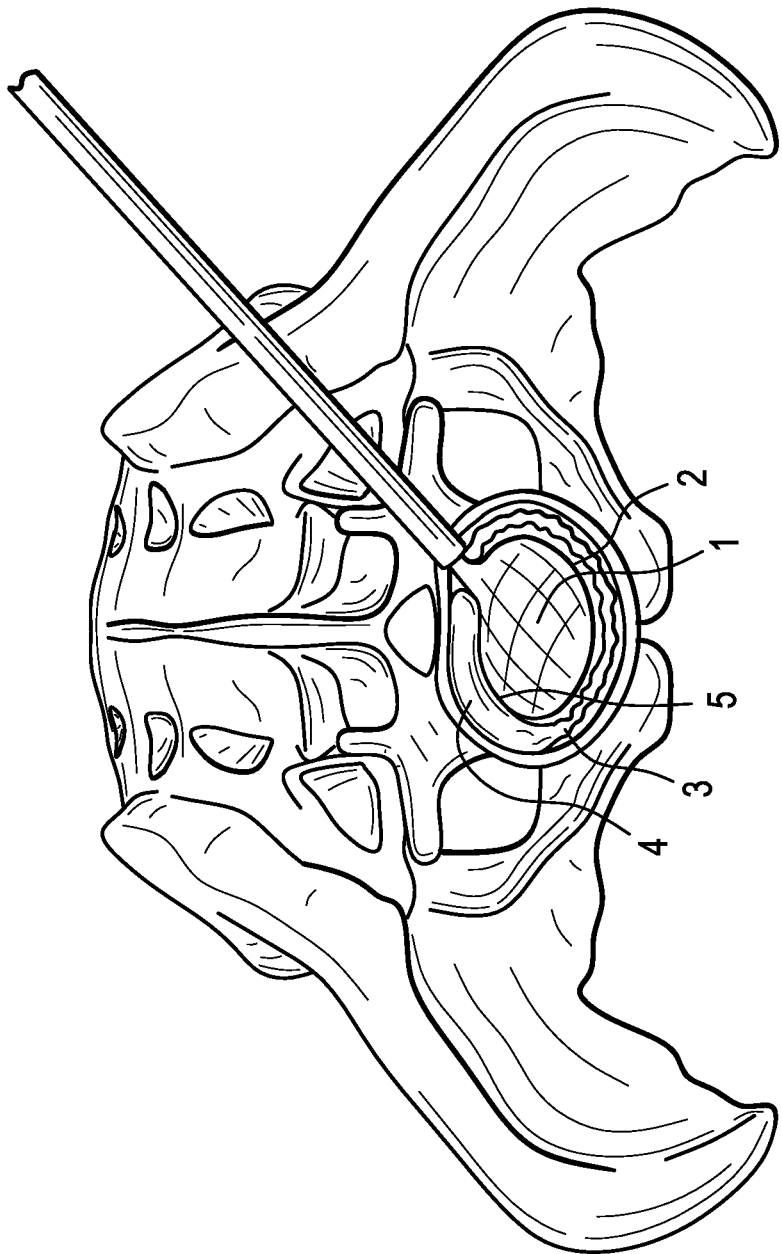

In a fourth step, and now referring to FIG. 1D, a curable material is flowed into the perimeter balloon. The balloon expands around the inflated central distractor to both reach circumferentially around the central distractor and to contact the vertebral endplates separated by the central distractor. In essence, the filled perimeter balloon and the filled central distractor take up all of the void space available within the interbody cavity. In some embodiments, the perimeter balloon is pre-inflated with a biologically inert fluid, such as saline, to verify the inflated position and the structural integrity of the perimeter balloon. The biologically inert fluid may have radiopaque additives in order to aid with visualization using fluoroscopy. The perimeter balloon is then either deflated and re-inflated with the curable material, or subjected to a controlled injection of curable material which replaces the initial fluid at a constant rate thereby maintaining the pressure and shape of the inflated perimeter balloon. Suitable curable materials may include two-component self-curing materials such as PMMA, silicone, urethane, epoxy, and acrylic resins (such as dental resins). A possible acrylic resin consists of a combination of BISGMA (bisphenol-A-glycidyl methacrylate) and TEGMA (tri ethylene glycidel methacrylate) mixed with a solution of BPO (benzoyl peroxide) in NMP (N-methyl-2-pyrrolidone) and a solution of DMPT (N,N-Dimethyl-p-toluidine) in PEGDA ~300 (polyethylene glycol diacrylate, Mn 258). Other suitable materials are disclosed in U.S. Pat. No. 9,333,091 B1, the relevant portion of the specification of which is incorporated herein. Other possible materials include composite materials using a supercooled metal, which is flowed into position with low stress and then intentionally stressed to solidify and fuse the metal particles, electrorheological materials, and magnetorheological material.

Figure 1E:
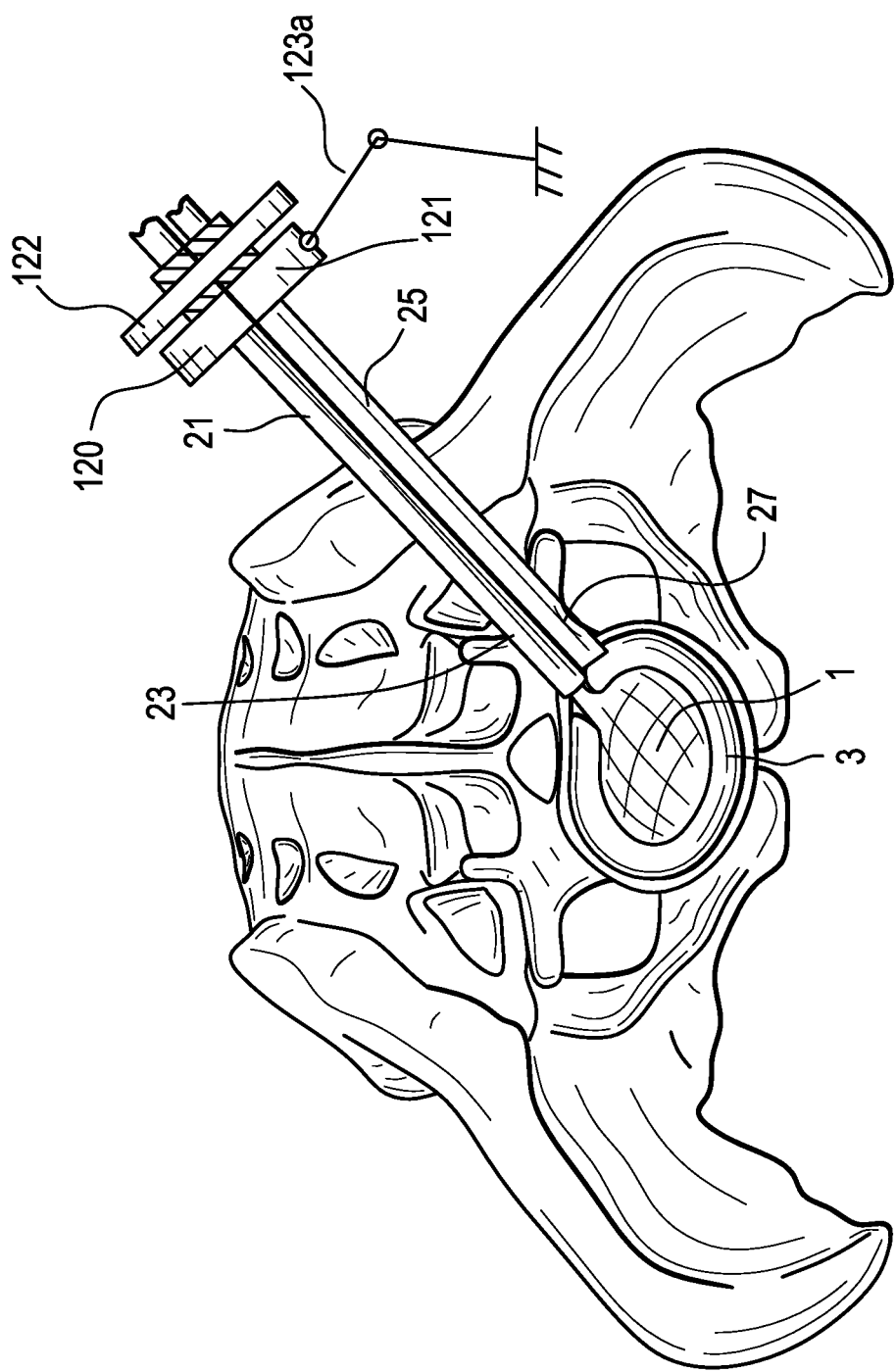

In a fifth step, and now referring to FIG. 1E, the surgeon waits while the curable material cures. In some cases, such as when a conventional PMMA is used, this waiting period may be 5-20 minutes. In some embodiments, the surgeon can accelerate the curing of the curable material by various energy means, including heat, chemical accelerants, light, electricity, moisture, or vibrations. In some embodiments, the curable material is not self-curing but will remain flowable until the external energy stimulus is employed to initiate curing. Such materials require application of a curing initiator such as radiation (such as light), heat, vibration, moisture, or electrical energy to effect curing. Possible materials include cyanoacrylates, one-part epoxies, heat-cured urethanes, single component silicones, and acrylic resins. One such resin uses CQ (camphoquinoione), NMP, 4EDMAB (ethyl 4-dimethlaminobenoate), and PEGDA. This resin polymerizes in blue light through the following mechanism: a photo-initiator is activated using excitation light; the active photo-initiator and tertiary amine (H donor) form free radicals; and the free radicals polymerize the monomer. Use of such curable materials provides unlimited flexibility and alleviates time pressures for adjusting components before curing. In accordance with a feature of the invention, the curable material may be a hybrid, i.e., one that primarily cures on-demand with an external stimulus but also employs a longer duration self-cure, meaning that the material will harden over time with or without the addition of material or energy, thereby ensuring that any fluid that remains unhardened in the initial cure will eventually harden. Possible materials include combinations of the self-cure and external energy-initiated materials listed above. One such chemical- and photo-initiated material uses a combination of BISGMA/TEGMA mixed with a solution of BPO, CQ, and NMP and a solution of 4EDMAB, DMPT, and PEGDA. In another embodiment, the curable material remains flowable only in the presence of an externally modified environment, such as heat or electrical current, and when the external input is removed (and the interbody space allowed to return to its natural state), the material hardens. Possible materials include materials with low melting temperatures or low glass transition temperatures. In still another embodiment, the curable material in the perimeter balloon may be cured by UV light transmitted through the central distractor. Other suitable inflation and curing materials and techniques, are disclosed in U.S. Patent Application Publication No. 20190008649, the relevant portion of which is incorporated by reference herein.

Figure 1F:
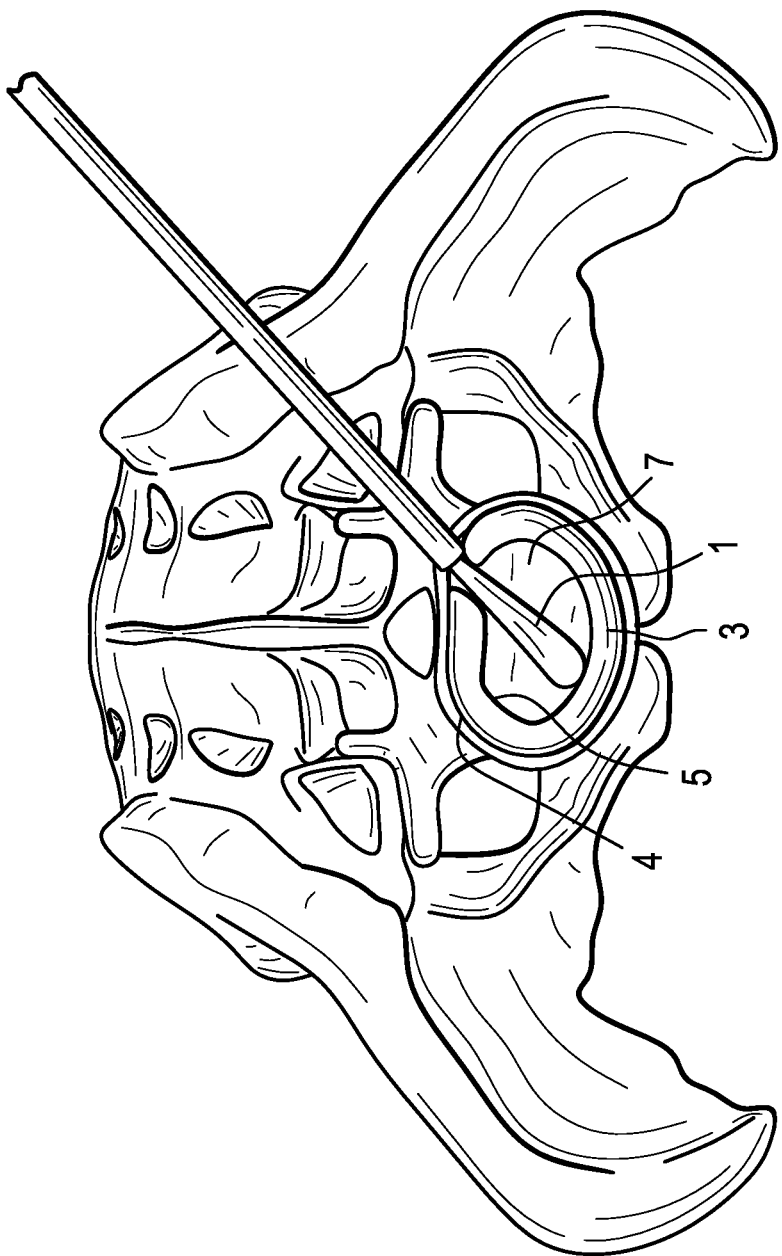

In a fifth step, and now referring to FIG. 1F, the material in the perimeter balloon is fully cured, and the central distractor is deflated.

Figure 1G:
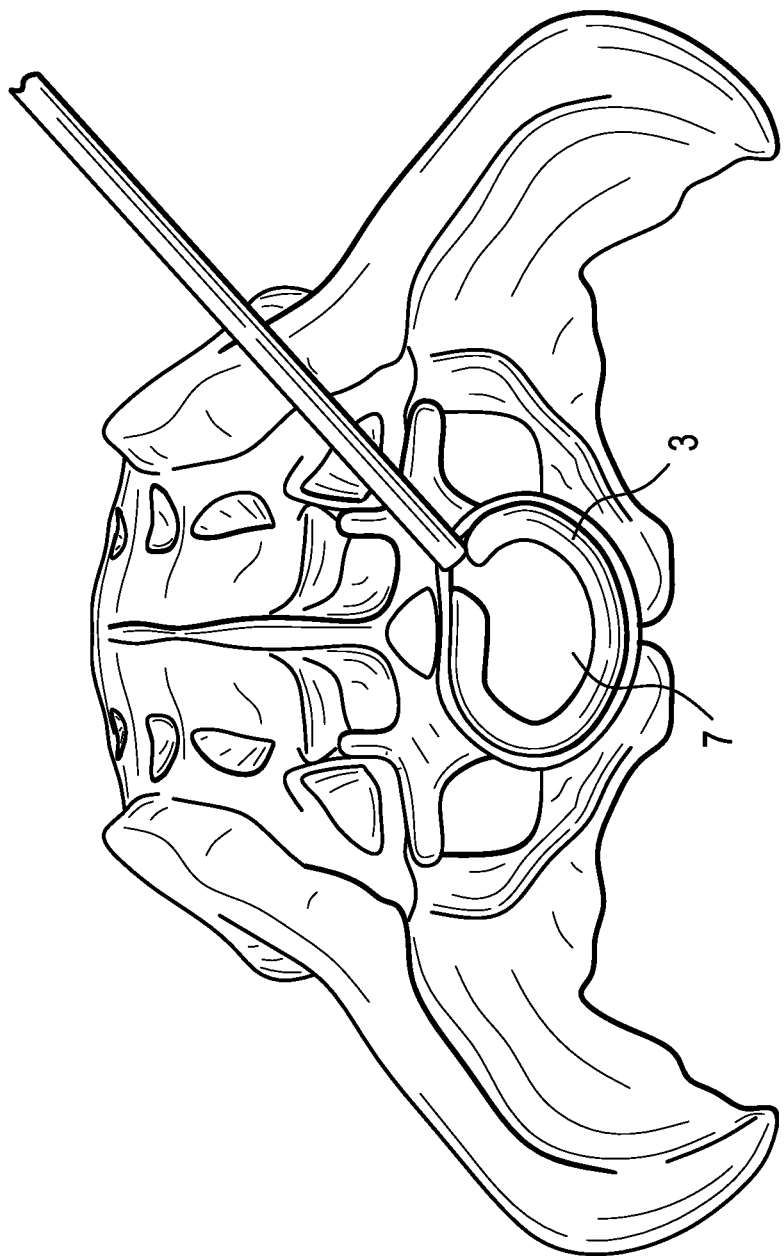

In a sixth step, and now referring to FIG. 1G, the deflated central distractor is withdrawn, thereby leaving a horseshoe-shaped structure supporting the disc space. This horseshoe provides support along the cortical rim of the vertebrae while leaving an access point to the center of the disc space. In some embodiments, the central distractor is not removed, but instead is made of a biocompatible or resorbable material.

Figure 1H:
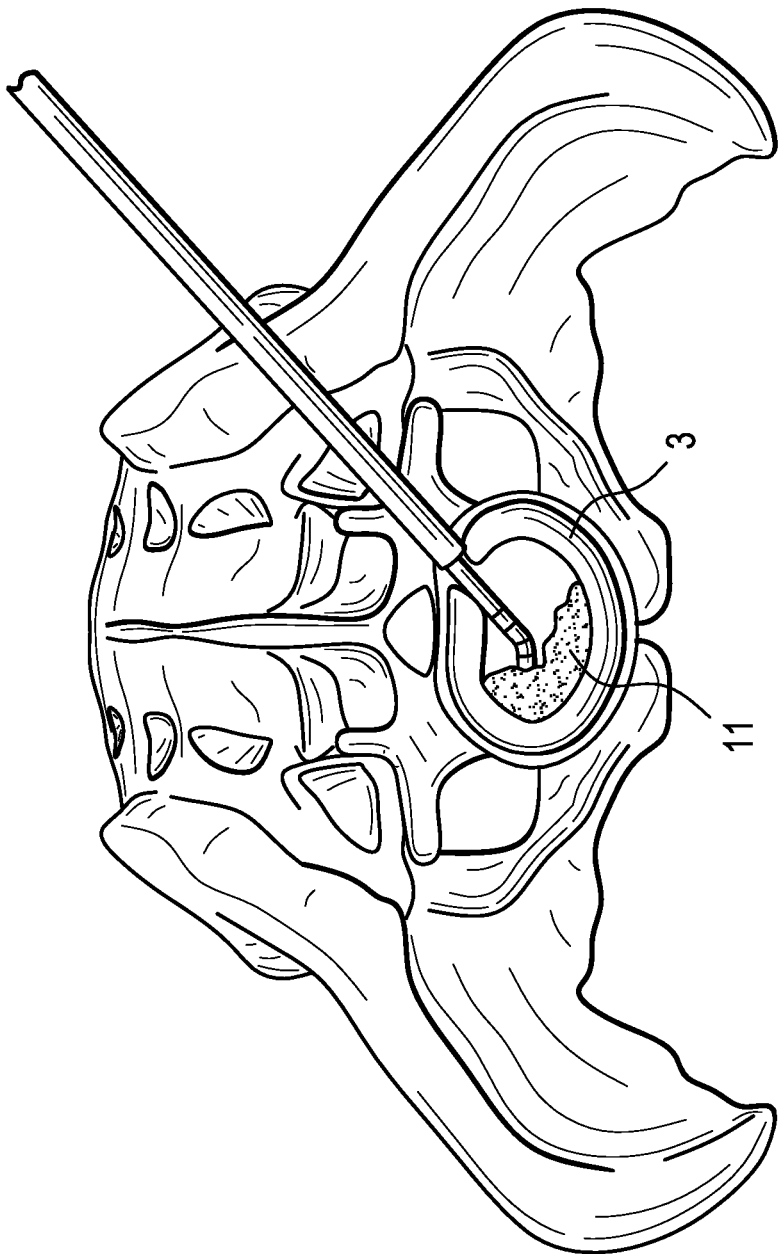

In a seventh step, and now referring to FIG. 1H, a tube is inserted through the access point produced in the sixth step and positioned near the center of the disc space. Graft material is then flowed through this tube and into the disc space, thereby filling the void with graft. In FIG. 1I, the graft fill tube is removed.

Figure 1J:
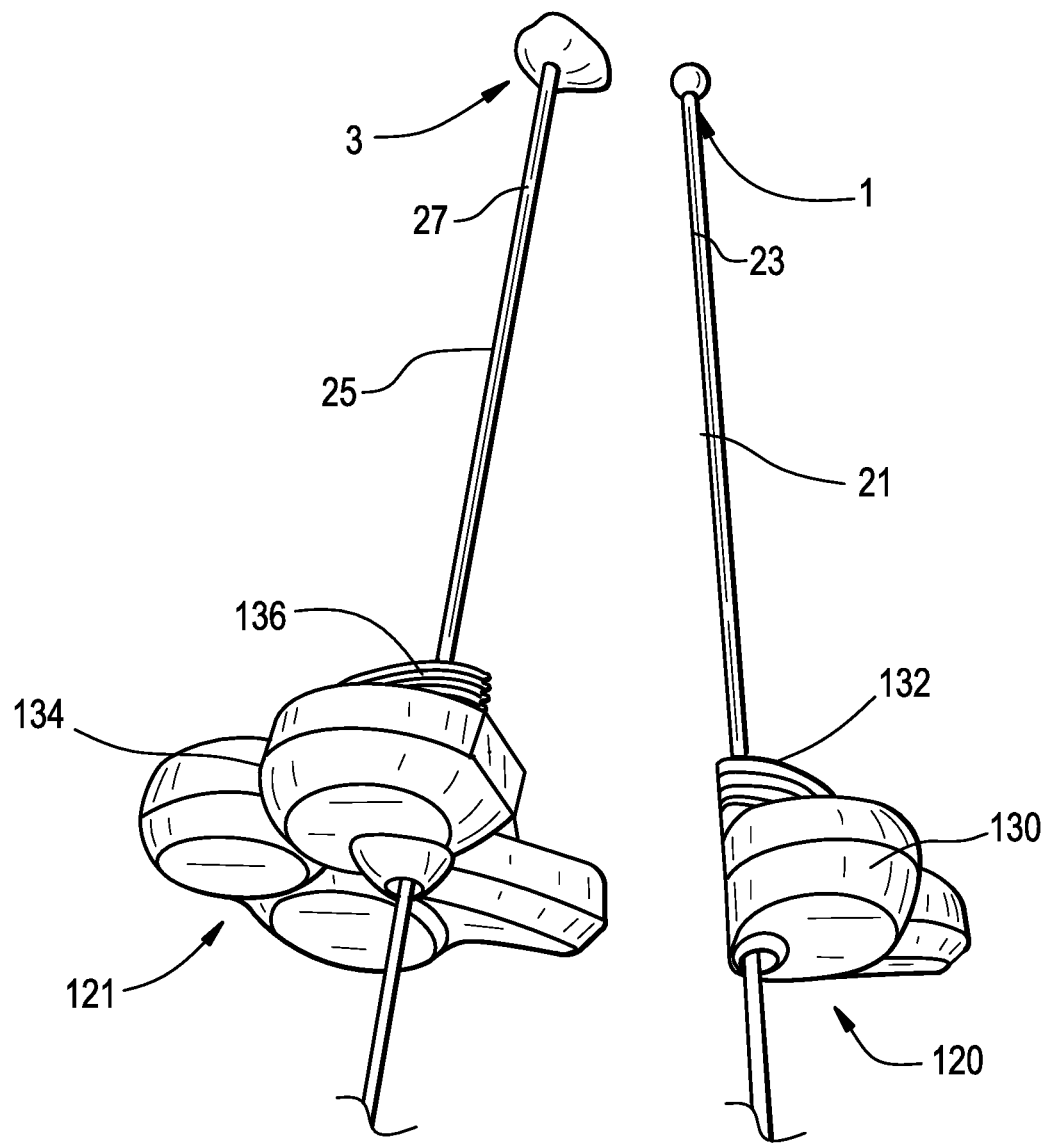

In accordance with an embodiment of the present invention and now referring to FIG. 1E, there is provided an instrument for forming an intervertebral fusion device. A distraction device includes a first tube 21 having a distal end portion 23 and an inflatable distractor 1, e.g., central balloon, attached to distal end portion 23 In the embodiment depicted in FIG. 1E, central balloon 1 is filled with a biologically inert fluid. In accordance with an aspect of the invention, a threaded connector 120 may be engaged with tube 21 near a proximal end portion. As illustrated in FIG. 1J, connector 120 may include a handle 130 and a threaded neck 132 extending from handle 130. A tube channel extends through handle 130 and neck 132 through which first tube 21 extends. The distraction device further includes a second tube 25 having a distal end portion 27 and an inflatable distractor 3, e.g., perimeter balloon, attached to distal end portion. In the embodiment shown in FIG. 1E, perimeter balloon 3 is filled with a curable material and has a height sized to span a disc space.

Figure 1K:
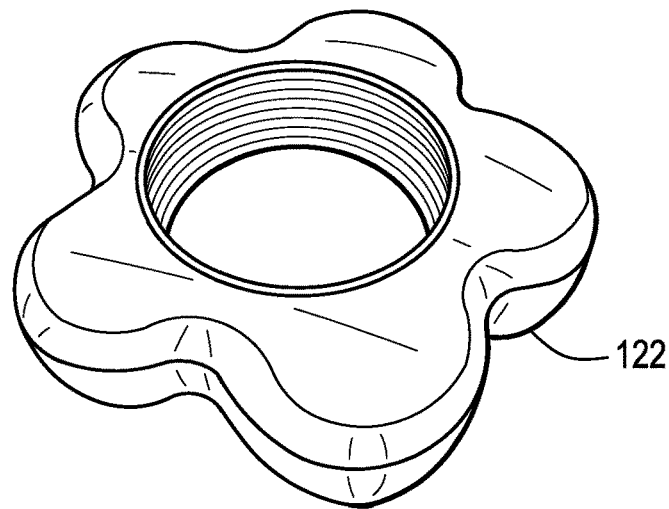
Figure 1L:
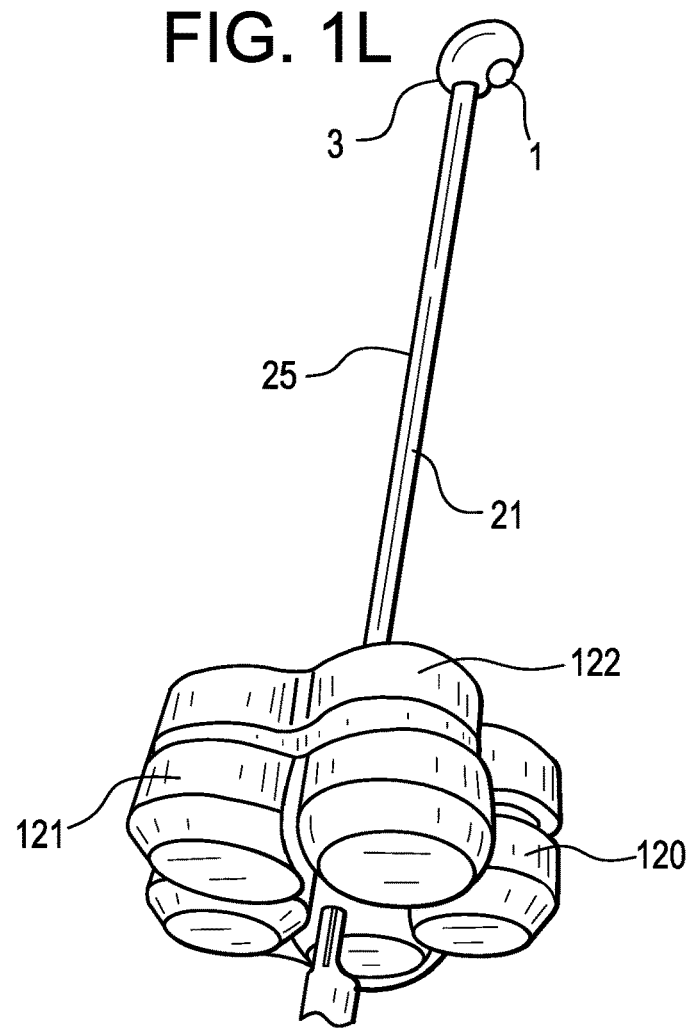

In accordance with an aspect of the invention, a threaded connector 121 may be engaged with second tube 25 near a proximal end portion. Similar to connector 120, connector 121 may include a handle 134 and a threaded neck 136 extending from handle 134. A tube channel extends through handle 134 and neck 136 through which second tube 25 extends. Connectors 120 and 121 are of a mating geometry such that when they are connected, their respective tube channels are adjacent to each other and tubes 21 and 25 are disposed adjacent to each other as illustrated in FIG. 1L. As illustrated in FIG. 1K, a threaded coupling component 122 is provided to couple with connectors 121 and 120 thereby rigidly attaching the proximal ends of first and second tubes 21 and 25. This arrangement fixes the position of central balloon 1 with respect to perimeter balloon 3 which keeps the relative position of the balloons stable regardless of the forces that they encounter in the disc space as they are inserted and inflated. Coupling component 122 may be removed after perimeter balloon 3 has hardened in order to remove the central balloon 1 and while maintaining perimeter balloon 3 in place.

In an alternate arrangement, connector 121 may engage a pair of tubes near their proximal end portions. The distal end of each tube may be connected to perimeter balloon 3 so that one tube may be used for injecting material into perimeter balloon 3 and the other tube may be used for removing material from perimeter balloon 3. In some embodiments, tube 25 may include two or more lumens.

In experiments it was observed that a substantially spherical or puck-shaped central balloon self-located in a stable manner to the central notch formed by the concave shapes of the upper and lower endplates. The perimeter balloon however, in absence of an anchoring mechanism, tended to eject out of the annulus in areas of missing or weak fibers. With a coupling mechanism between the central and perimeter balloons, the stability of the central balloon anchored the perimeter balloon into the correct location.

In some embodiments the distraction device may be locked or fixed to an external, stationary surface such as an operating room table or a location on a patient's body to help fix the position of central balloon 1 and perimeter balloon 3 in the disc space. In one embodiment, a lock arm 123 is provided which may attach to any of connectors 120 and 121, threaded coupling component 122 or tubes 21 and 25 and to a stationary surface 127. Lock arm 123 may include one or more lockable articulated leg segments 123a and 123b. Accordingly, lock arm 123 may be locked at any location and angle. It is believed that the lock arm 123 in conjunction with tubes 21 and 25 will fix the position of central balloon 1 and perimeter balloon 3 in the disc space and will prevent movement due to any forces during inflation and will help overcome any tendency of the balloons to eject out of the disc space entry hole or weak points in the disc annulus.

Referring to FIG. 1D, there is provided a balloon assembly for treating an intervertebral disc space, comprising: a) an inflated distractor 1 having an outer perimeter 2 and being sized to distract the intervertebral disc space, the inflated distractor filled with a biologically inert fluid, b) an inflated fusion balloon 3 forming a shape having an outer perimeter 4 and an inner surface 5, the fusion balloon filled with a curable material, wherein the balloon wraps around the distractor so that the inner surface of the fusion balloon contracts the outer perimeter of the inflated distractor, wherein the balloon forms an annular shape defining an inner space and the inflated distractor is disposed in the inner space.

In keeping with an aspect of the invention and now referring to FIG. 1F, there is provided a balloon assembly for treating an intervertebral disc space, comprising: a) a deflated distractor 1 having an outer perimeter, b) an inflated fusion balloon 3 forming a shape having an outer perimeter 4 and an inner surface 5 defining an inner space 7, the fusion balloon filled with a cured material, the fusion balloon 3 being sized to distract the intervertebral disc space, wherein the deflated distractor 1 is disposed within the inner space of the balloon.

One purpose of the inflatable distractor 1 is to, in conjunction with the fusion or perimeter balloon 3, distract the collapsed disc space to a desirable height that restores the physiologic spatial relationship of the adjacent vertebral bodies. The inflatable distractor. may be provided in a multiplicity of sizes to correspond to appropriate disc heights. In some expanded embodiments, the inflatable distractor has a cylindrical shape comprising an annular intermediate portion between two endfaces. In some expanded embodiments, the space within the annular intermediate portion is filled with a biologically inert distraction fluid, such as saline. In some embodiments, the inflatable distractor comprises a central balloon defined by a mesh bag that is inflated using osteogenic material and is not removed from the inner space. In some embodiments, this balloon or mesh bag is resorbable over time. The endfaces may have roughened outer surfaces or a high-friction coating or jacket, in order to better grip the vertebral endplates. In some embodiments, the endfaces are substantially parallel to each other in the inflated condition. In others, the endfaces are angled such that the expanded balloon takes on a wedged shape so that the height of the anterior portion of the expanded device is greater than the height of the posterior portion of the expanded device. This allows the device to restore lordosis when the interbody fusion device is used in either the lumbar or cervical regions of the spine. Preferably, the wedged shape produces an incline angle of between 5 and 20 degrees, more preferably between 5 and 15 degrees. In still others, the endfaces are angled such that the expanded balloon takes on a wedged shape along the coronal plan so that the lateral heights on either side of the center line of the expanded device are not equal. This allows the device to correct scoliosis and restore the straightness of the spine in the coronal plane. In some embodiments, the central balloon may be comprised of multiple compartments or balloons, of which the pressures are separately controlled and are used to restore the correct angles in at least one anatomical plane to the adjacent vertebral endplates relative to each other, providing better spinal alignment.

In at least one embodiment, the fusion device includes a perimeter balloon of at least two compartments and a central balloon of at least one compartment. Accordingly, when the pressures are separately controlled for each compartment, the fusion device has full adjustability in 3 dimensions, linearly along the caudal-cranial axis and rotationally around both the anterior-posterior axis and transverse axis.

In any of the disclosed embodiments, the central inflatable distractor may be made from the balloon materials disclosed in US Patent Application Publication No. 20040230309, the relevant portion of the specification of which is incorporated by reference. The central inflatable distractor may be made with a method that uses an intermediate sized lumen, forms one end into a larger balloon by pressurizing the lumen inside of a mold, and then compresses the other end into a small size (able to fit through a small diameter cannula) either by folding the excess material or by reflowing into a small diameter lumen and trimming the excess material.

The perimeter balloon can be made of any conventional material used for medical balloons. In some embodiments, it can be nonporous. In other embodiments, it can be porous to allow some cement to escape and thereby bond the support to the adjacent tissue. In some embodiments, the perimeter balloon is resorbable over time. The upper and lower surfaces of the perimeter balloon may have roughened outer surfaces in order to better grip the vertebral endplates. These roughened outer surfaces may include for example, a plurality of teeth. In other embodiments, it can be enclosed in a stent or other porous or osteoconductive jacket, which will provide a surface for bone to grow through and around, thereby adding additional stability to the implant. In some embodiments, the stent or porous jacket is made of osteogenic material. In other embodiments, it is made of metal, shape memory material such as nitinol, polymer, or other robust material. In some embodiments, the perimeter balloon may be comprised of multiple compartments or balloons, of which the pressures are independently controlled and are used to restore the correct angles to the adjacent vertebral endplates relative to each other, providing better spinal alignment. The perimeter inflatable device may be made with a method that uses an intermediate sized lumen, forms one end into a larger balloon by pressurizing the lumen inside of a mold, and then compresses the other end into a small size (able to fit through a small diameter cannula) either by folding the excess material or by reflowing into a small diameter lumen and trimming the excess material.

In one embodiment, the perimeter balloon is made of an elastic material. This allows the balloon to be form-fitting as it expands into the space between the central inflatable distractor and the surviving annulus fibrosus. In other embodiments, the balloon is inelastic and forms a predetermined shape when inflated. Such an inelastic balloon may be beneficial because the predetermined shape can be a horseshoe shape, and thereby allow the structural support to extent around the perimeter of the central inflatable distractor and rest upon the cortical rim. It may also be beneficial because the predetermined shape may include either parallel endfaces or endfaces with angles relative to each other, and thereby allow the perimeter balloon to contribute to the final vertebral distraction and relative positioning.

Figure 15:
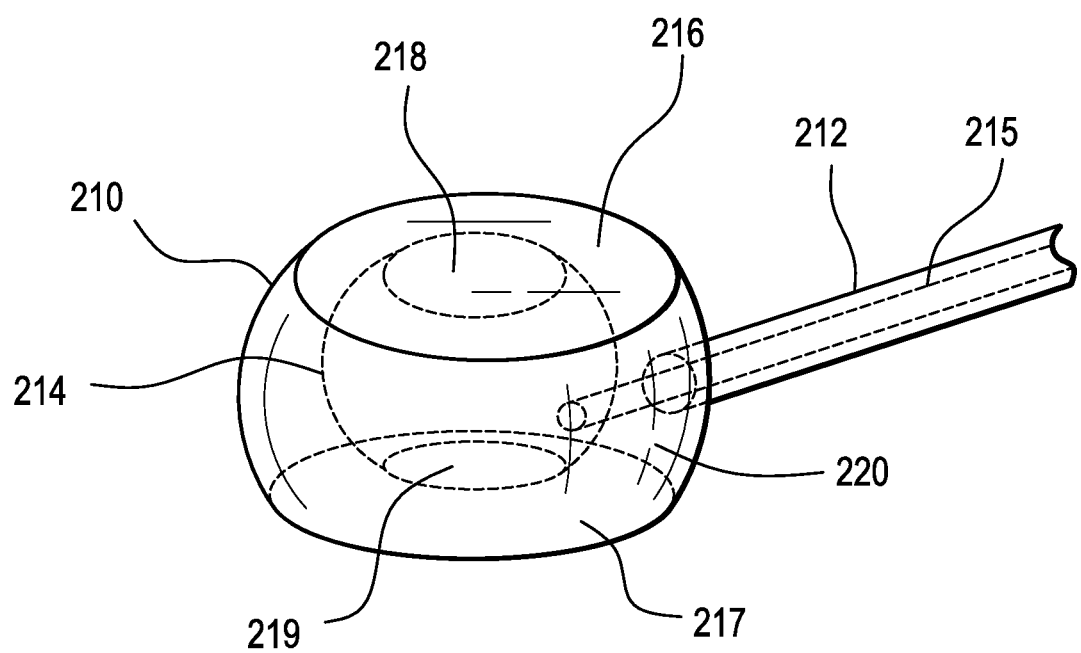
FIG. 15 depicts an intervertebral fusion device in accordance with an embodiment of the invention.

In another embodiment, the central balloon may be completely contained within a larger balloon as illustrated in FIG. 15. In this embodiment, an external balloon 210 may be made from compliant or non-compliant material. External balloon 210 may be connected to a lumen 212 and expanded to fill an interbody space by inflating with either biologically inert fluid such a saline or with a hardenable material through the space between lumen 212 and lumen 215. External balloon 210 includes an upper wall 216 having an external surface and an internal surface and a lower wall 217 having an external and internal surface. In one embodiment external balloon 210 expands enough to contact any remaining annulus along its outer circumference thereby taking the shape of the emptied out interbody cavity. The external surface of the upper wall 216 contacts the superior vertebral endplate and the external surface of lower wall 217 contacts the inferior vertebral endplate. In keeping with the invention, an internal balloon 214 is fully enclosed in external balloon 210. Internal balloon 214 is connected to lumen 215 through which it is inflated with biologically inert fluid such as saline. Internal balloon 214 is made from a non-compliant material and sized such that when it is expanded it contacts the internal surface of balloon wall 216 and contracts the internal surface of lower balloon wall 217. The horizontal footprint of the interior balloon is smaller than the horizontal footprint of the exterior balloon such that there is a horseshoe-shaped space 220 between them. Space 220 is eventually filled with hardenable material and cured in order to provide a rigid fusion support at the vertebral cortical rim.

Lumen 215 will provide a port to introduce osteogenic material into the central balloon. The balloon material may be cut or dissolved out of the inner space after the material in space 220 is cured to access the endplates for fusion or the balloon material may be resorbable over time.

In other embodiments, the perimeter balloon forms a substantially horseshoe-shape. The horseshoe shape is advantageous because it provides for a large surface area to rest upon the cortical rim of the adjacent vertebral bodies, and its open end allows for both withdrawal of the central deflated distractor and delivery of the bone graft into the inner space. Preferably, the perimeter balloon is made of a shape memory material that takes on the shape of a horseshoe in its relaxed configuration. In other embodiments, however, the horseshoe shaped perimeter balloon is made of a conventional polymer having no shape memory characteristics, and the balloon is simply manually curled around the central inflatable distractor prior to its delivery into the disc space, so that when the perimeter balloon enters the disc space, it already has a substantially horseshoe shape. In other embodiments, the perimeter balloon is introduced separately from the central balloon, but guidelines guide the perimeter balloon to wrap around the central balloon in a substantially horseshoe shape.

In these horseshoe-shaped embodiments, the curable material may be introduced into the perimeter balloon by a third tube whose distal end is located within the perimeter balloon. The distal end of this third tube is initially fully inserted into the perimeter balloon and begins by filling the distal portion of the perimeter balloon. As curable material fills the distal portion of the perimeter balloon, the distal end of the third tube is withdrawn proximally from the perimeter balloon at the same rate as the rate of fill. This third tube thereby insures the complete filling of the perimeter balloon. In other embodiments, the curable material is simply flowed freeform into the proximal end opening of the perimeter balloon and allowed to fill the perimeter balloon.

Figure 2:
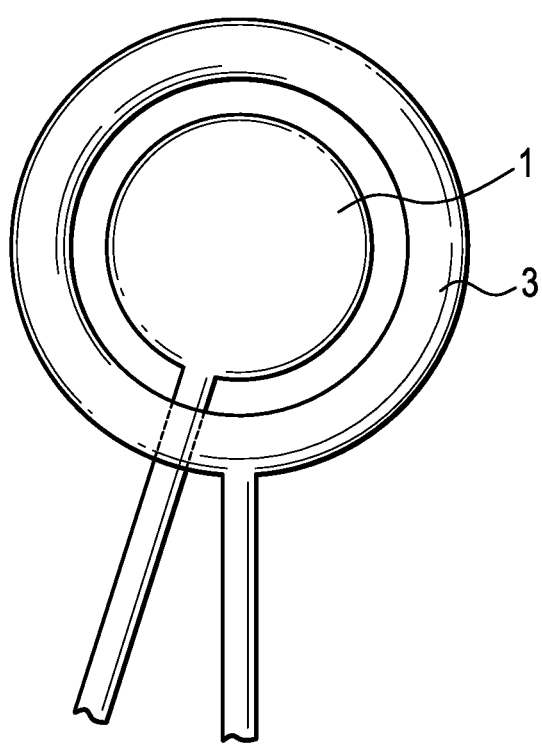
FIG. 2 illustrates an annular perimeter balloon of the present invention.

In one embodiment, the perimeter balloon forms an annular shape. An annular perimeter balloon can be accomplished with the technology disclosed in Stalcup's FIG. 4. The Stalcup technology would need to be simply modified by adding a central inflatable distractor at the distal end of Stalcup's first fill hose. Such an annular embodiment is shown in FIG. 2 herein. The annular perimeter balloon possesses a hole that allows for passage and withdrawal of both the central inflatable distractor and a graft fill tube. The advantage of an annular balloon is that it provides slightly more surface area contact with the vertebral bodies than the horseshoe shaped perimeter balloon, thereby reducing the stress upon the structural support. It also provides for more even support, thereby reducing stress heterogeneities.

In some embodiments, the system can be used without a perimeter balloon, thereby allowing the cement to completely conform to the remaining anatomy. In this embodiment, a catheter could be used to evenly deposit the curable material. This catheter can be steerable and independent of the central balloon or guided by the circumference of the central inflatable distractor via a guidance system around the central inflatable distractor can also be used to guide tools and implants into the disc space. These tools can be used to inspect the disc space, perform additional disc and annulus removal, and place implants. In another embodiment, an expanding foam containing curable material may be used in place of the perimeter balloon. These configurations may not be preferred because they rely on a substantially intact and strong annulus to contain the pressure of the expanding perimeter distraction means.

In some embodiments, the system can be used without a central balloon, instead using the perimeter balloon for the entirety of the distraction prior to curing it. In this configuration, the balloon would be made of an inelastic material to ensure that an inner cavity is formed to be packed with bone graft. In some embodiments, the perimeter balloon forms a central sealed cavity in which pressurized fluid or gas may be injected to add distraction force to the endplates.

The curable substance that fills the perimeter balloon forms a structural material capable of withstanding the physiologic axial loads of the spine. In some embodiments, the curable material may be a conventional bone cement, such as a PMMA cement, or a foaming bone cement. In other embodiments, the curable material may be a low viscosity cement similar to common dental cements, which gives the advantage of being able to flow the curable substance easily through small lumens. In some embodiments, the curable material self-curing from a chemical reaction when multiple components are mixed and will harden when mixed after a set amount of time. In others, it will be cured in a reaction with light or other energy input and will only cure when the external stimulus is applied, giving the advantage of extending the amount of time in which to set the balloons in a desirable position, but decreasing the cure time once the cure process is elected to start. In a preferred embodiment, the curable substance will employ a combination of self-cure and external energy cure, giving the advantage of greater control over the cure time while ensuring that all material eventually hardens whether exposed to the eternal stimulus or not.

The graft that is deposited within the inner space can be any osteogenic material suitable for fusing bone. The quantity of graft needed to fill the inner space may be estimated from the volume of fluid in the central distractor in its inflated configuration. This allows the surgeon to prepare the proper amount of graft and avoid over- or under-packing the inner space.

The delivery method and implant described herein may be suitable for both complete and partial discectomy (i.e., with annulus and ligament intact).

In some embodiments, it may be convenient to house each of the tubes associated with the balloon within a larger cannula. Housing these tubes within this larger cannula may ease the minimally-invasive insertion of the tubes into the patient. Therefore, in accordance with the present invention, there is provided a delivery cannula having a proximal end portion and a distal end portion;

wherein each tube is substantially received in the delivery cannula so that the distal end of the first tube projects from the distal end of the delivery cannula, and the distal end of the second tube projects from the distal end of the delivery cannula.

In some embodiments, no delivery cannula will be employed; a guidance system, such as an over-the-wire guidewire, can be used instead. The balloons will be inserted following the guidance system to ensure they pass only through the desired anatomical path without damaging nerves or other delicate anatomy. In some embodiments, the inflation devices will need protective sheaths to prevent damage as they are inserted into the disc space. The benefit of not using a delivery cannula is that you can minimize the outer diameter of components passing through the body into the disc space, thereby decreasing invasiveness. The over-the-wire entry may be used with any approach, such as anterior, lateral, posterior, or through Kambin's triangle.

In some embodiments, the graft material may be HEALOS FX™, a flowable collagen-based material available from DePuy Spine of Raynham, Mass., USA.

In some embodiments, the graft material may comprise a bone forming agent. In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-.beta. superfamily, including TGF-.beta.1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are administered into the target disc space. In some embodiments, between about 1 microgram (m) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft, xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 µm, for example, between about 50 and about 250 µm. In yet other embodiments of the present invention, in situ porosity is produced in the injected matrix to produce a porous scaffold in the interbody space. Once the in-situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. In some embodiments, the cement is selected from the group consisting of calcium phosphate, tricalcium phosphate and hydroxyapatite. In other embodiments, the cement is any hard, biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in-situ formation of a mineralized collagen composite. In some embodiments, the injectable precursor fluid comprises: [0085] a) a first formulation comprising an acid-soluble type I collagen solution (preferably between about 1 mg/ml and about 7 mg/ml collagen) and [0086] b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, Biomaterials 24: 4881-4890 (2003), the specification of which is incorporated herein by reference in its entirety.

Alternatively, the in-situ mineralization of collagen could be achieved by an increase in temperature achieved by other types of reactions including, but not limited to, chemical, enzymatic, magnetic, electric, vibration, focused ultrasound, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or bone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-.beta. or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In all cases, excess bone marrow aspirate can be collected and mixed with added graft extenders including collagen like the HEALOS™, and HEALOS FX™, each of which is available from DePuy Spine Inc, Raynham, Mass., USA.

Figure 3A:
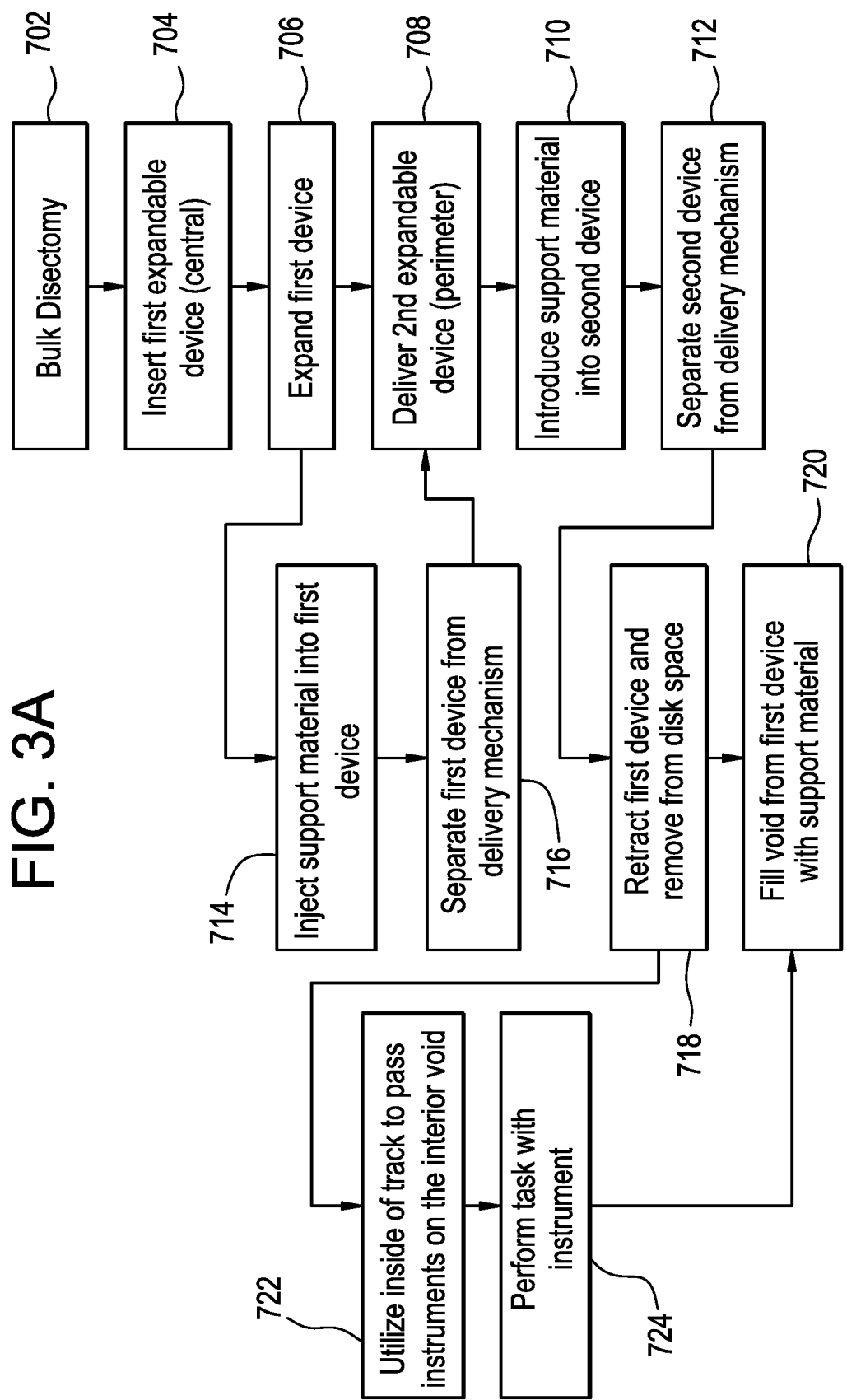
FIGS. 3A and 3B depicts flow charts for delivery methods.

Now referring to FIG. 3A, there is provided a flow chart of some preferred methods of carrying out the present invention. In general, this figure discloses the steps of: removing disc tissue to create a disc space (702) (bulk discectomy); inserting the central inflatable distractor into the disc space (704); expanding the central inflatable distractor (706); inserting the perimeter balloon into the disc space (708); introducing a curable material into the perimeter balloon (710), and separating the perimeter balloon from its second delivery tube (712).

In step 706 above, the step of expanding can include injecting a flowable support material (instead of saline) into the central inflatable distractor (714). The flowable support material can be selected from the group consisting of graft, hydrogels, curable materials, artificial disc materials, autograft and allograft. This injecting step can be followed by a step of separating the central inflatable distractor from its (first) delivery tube so that it may remain in the disc space (716).

In some embodiments, after step (712), there may be a further step (718) of retracting the central inflatable distractor and removing it from the disc space to create an inner space. In one embodiment, step (718) may be followed by a step of filling the inner space with a flowable support material (720). The flowable support material can be selected from the group consisting of graft, hydrogels, curable materials, artificial disc materials, autograft and allograft.

In another embodiment, removal of the central inflatable distractor (step 718) may be followed by: passing an instrument into the inner space (722), and performing a task with the instrument (724).

The passing of the instrument into the inner space may be accomplished by utilizing a track located upon the inner face of the perimeter balloon. The instrument may be selected from the group consisting of a camera, a light, a scraper, suction irrigation, a rasp, a knife, grasping, a burr, and a rotary cutter. The task may be selected from the group consisting of inspection, disc removal, and endplate preparation. Performance of the task may be followed by a step of a) filling the inner space with a flowable support material.

The perimeter balloon may then be separated from its delivery tube by cutting, unscrewing or breaking away.

Figure 3B:
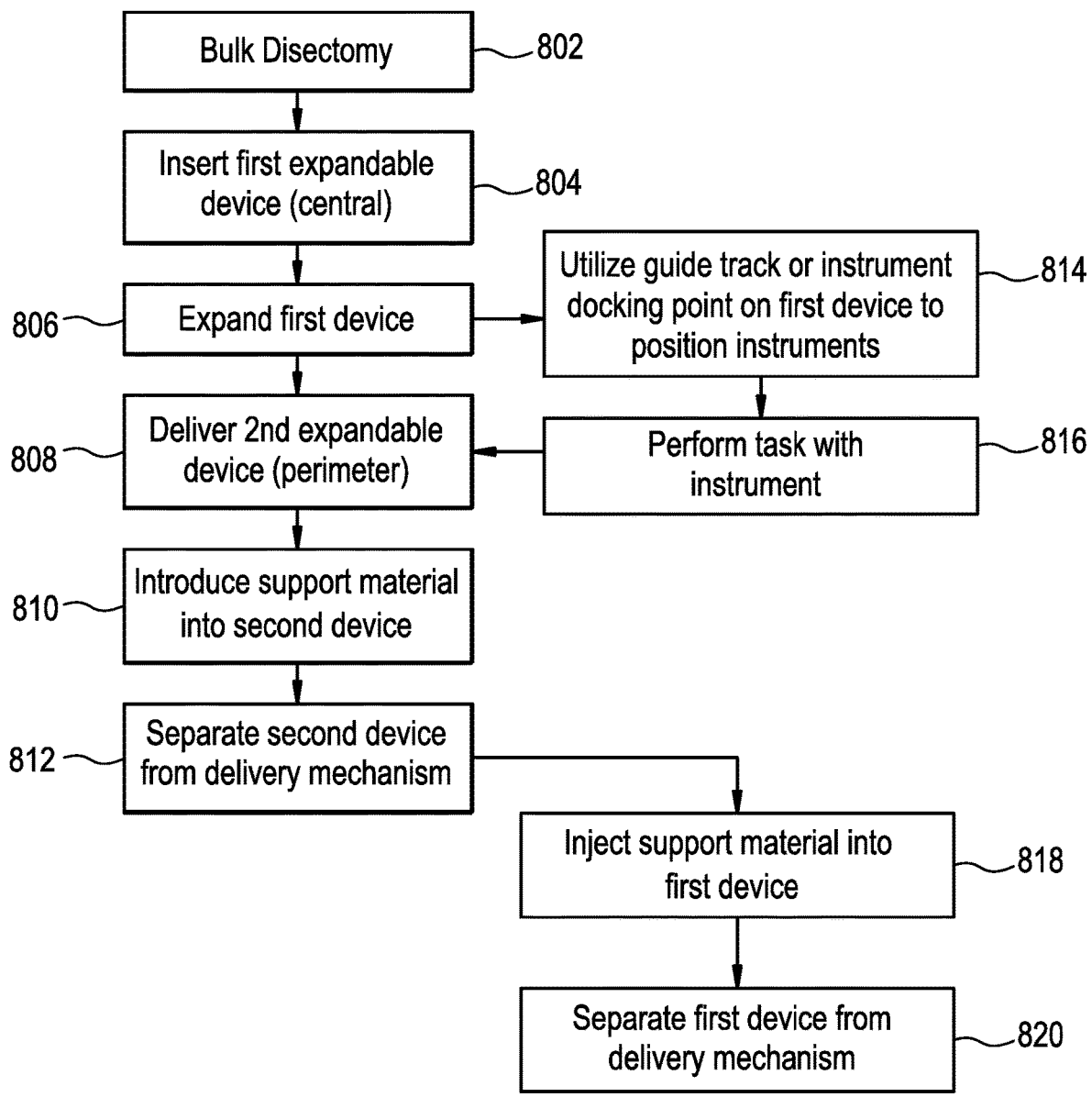

Now referring to FIG. 3B, there is provided a flow chart of some other preferred methods of carrying out the present invention. In general, this figure discloses the steps of: removing disc tissue to create a disc space (bulk discectomy) (802); inserting the central inflatable distractor into the disc space (804); expanding the central inflatable distractor (806); inserting the perimeter balloon into the disc space (808); introducing a curable material into the perimeter balloon (810), and separating the perimeter balloon from its second delivery tube (812). Expanding the central inflatable distractor (step 806) may be followed by: passing an instrument into the disc space (814), and performing a task with the instrument (816).

The passing of the instrument into the disc space may be accomplished by utilizing a track located upon the outer face of the central inflatable distractor. Instruments can be passed on both sides of the central inflatable distractor. The instrument may be selected from the group consisting of a camera, a light, a scraper, suction, irrigation, a rasp, a knife, grasping, a burr, and a rotary cutter. The task may be selected from the group consisting of inspection, disc removal, endplate preparation, cutting the annulus, cutting the ALL, cutting the PLL, and direct decompression. Performance of the task may be followed by step d) inserting the perimeter balloon into the disc space. The delivery of this balloon may also be accomplished by use of the track.

The curable material of step (810) can be selected from the group consisting of graft, hydrogels, curable materials, artificial disc materials, autograft and allograft.

The separation of step (812) can be accomplished by cutting, unscrewing or breaking away a section.

In some embodiments, the separation of step (812) can be followed by: injecting a support material into the first device (818).

The support material of step (818) can be selected from the group consisting of graft, hydrogels, curable materials, artificial disc materials, autograft and allograft.

In some embodiments, the injection of step (818) can be followed by separating the central inflatable distractor from its delivery tube (so that it may remain in the disc space) (820).

Figure 3C:
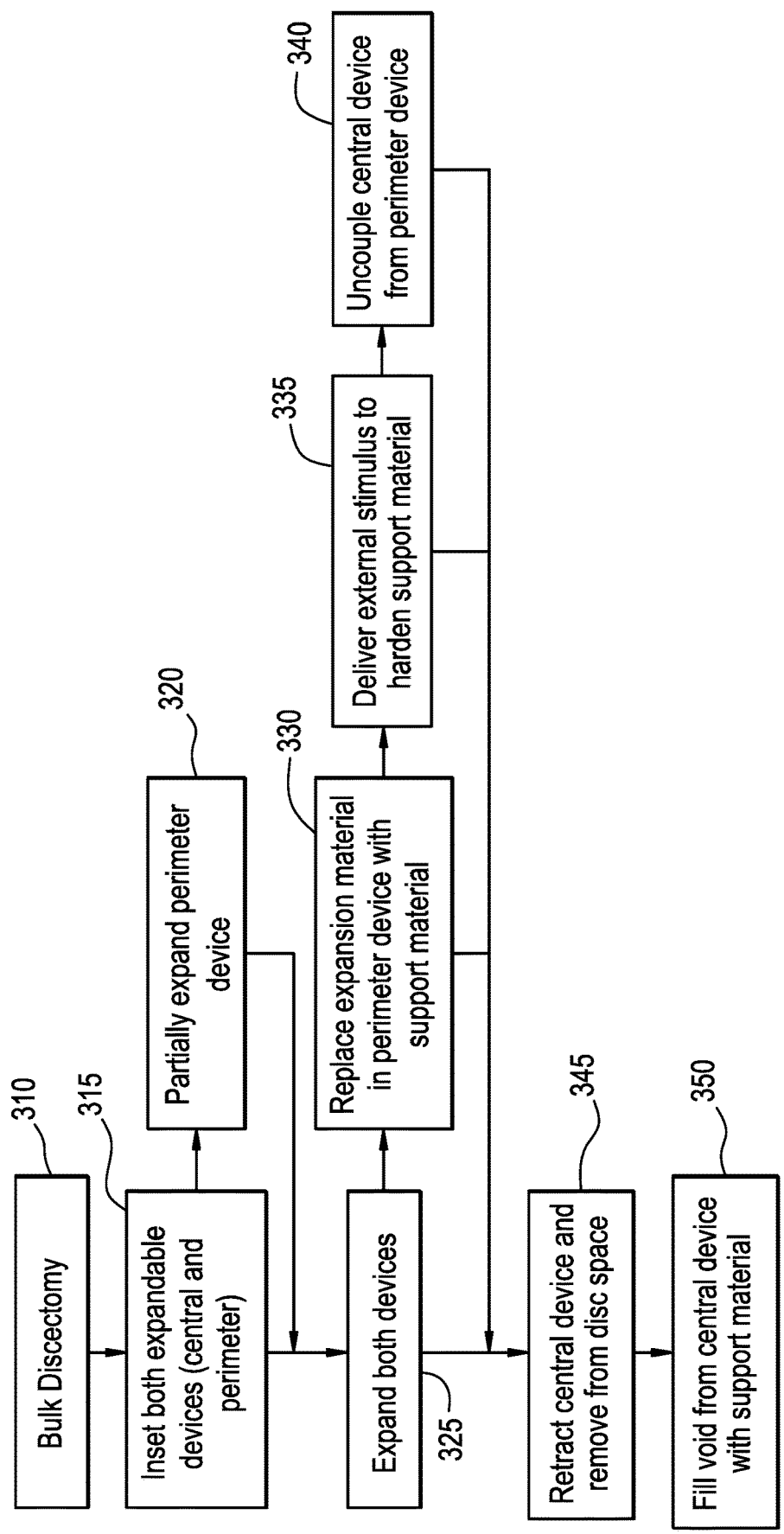
FIG. 3C illustrates a flow chart for delivery methods of the present invention.

An embodiment of a method of forming an interbody fusion cage in accordance with the invention is set forth in FIG. 3C. The method includes, in step 310 performing a bulk discectomy, i.e. removing disc tissue to create a disc space. In step 315, an expandable perimeter device and an expandable central distractor device are inserted into the disc space. In some embodiments the expandable perimeter device and expandable central distractor device may be simultaneously inserted and in other embodiments serially inserted. In some embodiments, the expandable central distractor includes a first tube having a distal end portion and an inflatable central distractor attached to the distal end portion of the first tube. Likewise, the expandable perimeter distractor includes a second tube having a distal end portion and an inflatable perimeter distractor attached to the distal end portion of the second tube. In some embodiments, the distal ends of the central distractor tube and the perimeter distractor tube are coupled together after step 315.

In one embodiment the perimeter device and the central device may be simultaneously or stepwise expanded in step 325. Alternatively, the perimeter device may be partially expanded with a biologically inert expansion material as in step 320 prior to step 325 to lower the risk of pinch points caused when the central device is expanded. In step 330, expansion material in the perimeter device may be replaced with support material. In some embodiments, the perimeter device may then be subject to external stimuli to harden the support material in step 335. In embodiments, where the central and perimeter device are coupled together, they may then be uncoupled in step 340.

In some embodiments, in step 345, the central device may be retracted and removed from the disc space after step 340. In other embodiments the central device may be removed from the disc space directly after step 325. The void created by removal of the central device may then be filled with support material in step 350.

Figure 4:
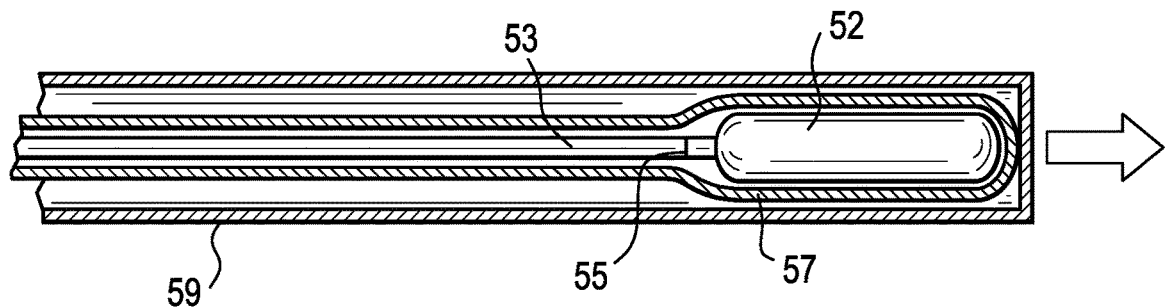
FIG. 4 shows a cross-section of an MIS delivery of a deflated balloon having a track.

Now referring to FIG. 4, there is provided an embodiment of a balloon having a track associated therewith. Balloon 52 is connected to balloon catheter 53 via connection/release point 55. A track 57 wraps around the periphery of the balloon. This apparatus is disposed within a delivery cannula 59.

Figure 5:
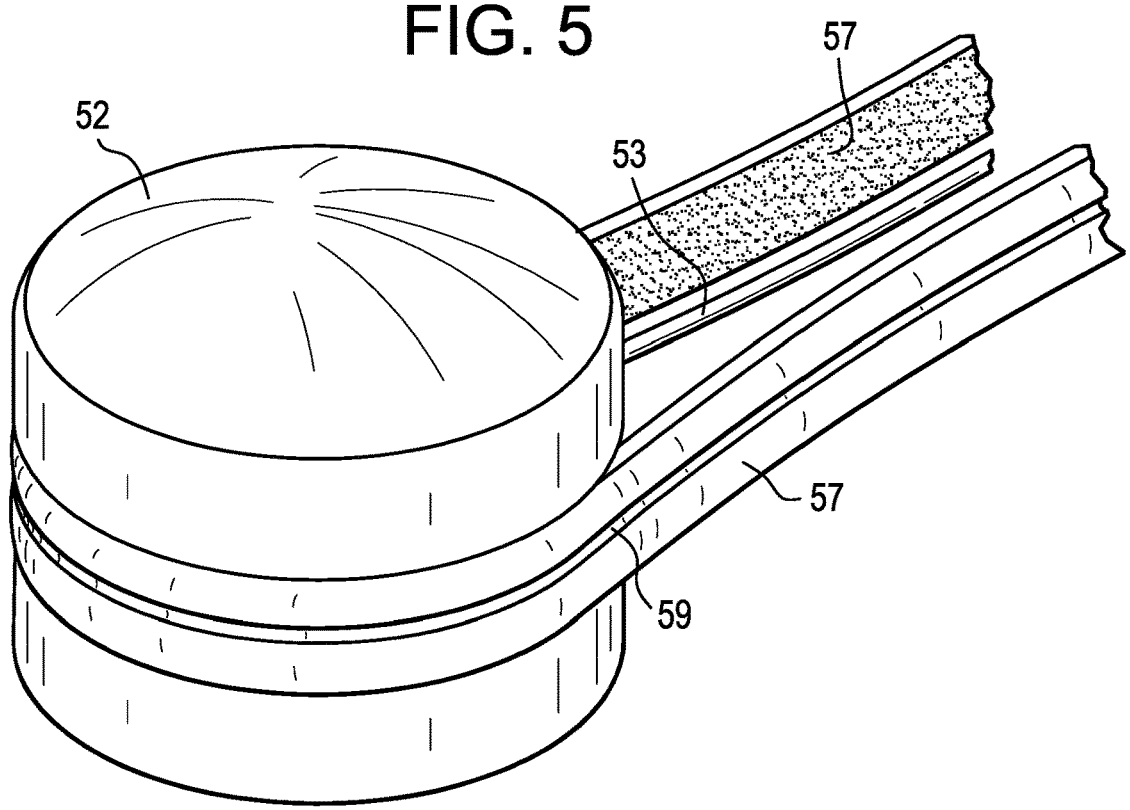
FIG. 5 shows a perspective view of an inflated balloon having a track.

Now referring to FIG. 5, there is provided a perspective view of a deployed balloon 52 having a track 57. Balloon catheter 53 extends from the proximal portion of the balloon. Track 57 has a central groove 59 for docking with an instrument. In some embodiments, track 57 may also be used for introducing and accurately positioning the perimeter balloon; the concave nature of the vertebral endplates will cause an inflated or partially-inflated central distractor to self-centralize in the disc space and will provide anchoring stability when perimeter balloons are inserted.

Figure 6A:
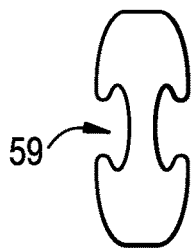
FIGS. 6A-6C depicts cross-sections of tracks.
Figure 6B:
Figure 6C:
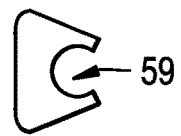

FIGS. 6A-6C disclose different track cross sections. FIG. 6A discloses a dual-sided track. FIG. 6B discloses a one-sided track. FIG. 6C discloses a track having a trapezoidal cross-section.

Figure 7:
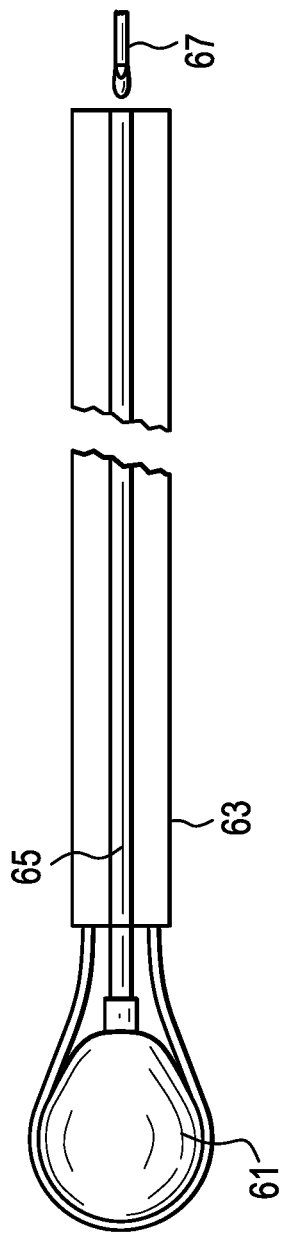
FIG. 7 illustrates a balloon used as a light source.

FIG. 7 discloses an embodiment in which the central balloon 61 is used as a light source. The balloon is attached to a light-transmitting catheter 65 that is housed within a delivery catheter 63. Light is transmitted from light source 67 into the light-transmitting catheter 65 and then into the balloon 61. In some embodiments, the fluid used to inflate the central balloon can include light-reflecting particles (not shown), such as titanium dioxide, in order to better disperse the light. The light allows for easier inspection of the disc space. In some embodiments, the light is used to cure the hardenable material in the perimeter balloon.

Figure 8:
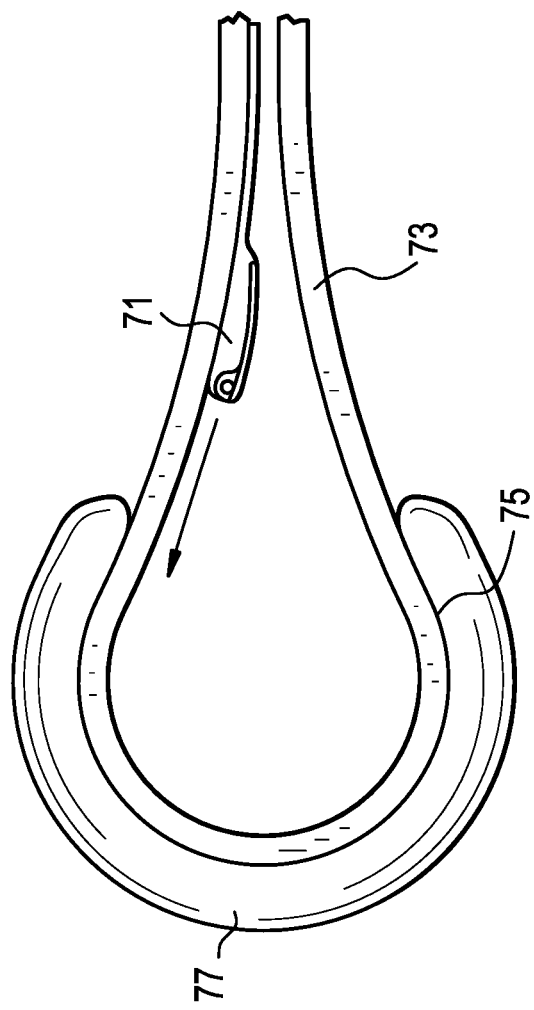
FIG. 8 depicts an assembly for passing instruments into the inner space.

FIG. 8 discloses a step of passing an instrument 71 into the inner space via a track 73 located on an interior surface 75 of the perimeter balloon 77.

Figure 9B:
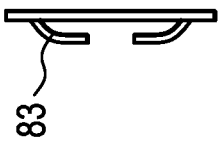
FIGS. 9B-9E shows cross-sections of cutouts of FIG. 9A.
Figure 9A:
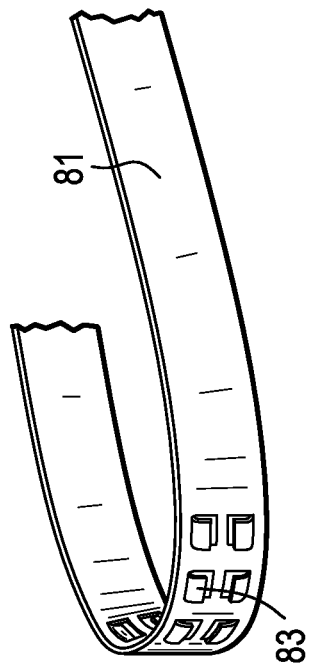
FIG. 9A shows a track having cutouts.
Figure 9E:
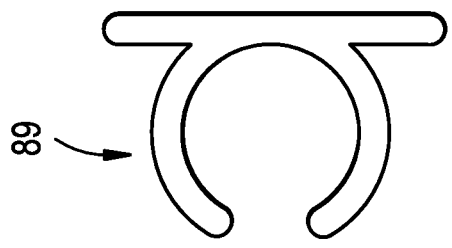
Figure 9D:
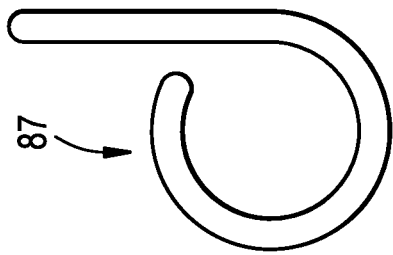
Figure 9C:
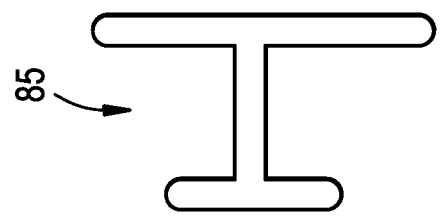

FIG. 9A discloses an embodiment of a track 81 that has cut-outs 83. These cutouts provide a means for securing the instrument. FIG. 9B discloses a cross-section of cutout 83. FIG. 9C discloses a cross-section of a T-Track cutout 85. FIG. 9D discloses a cross-section of a rolled-track cutout 87. FIG. 9E discloses a cross-section of a C-track cutout 89.

Figure 10:
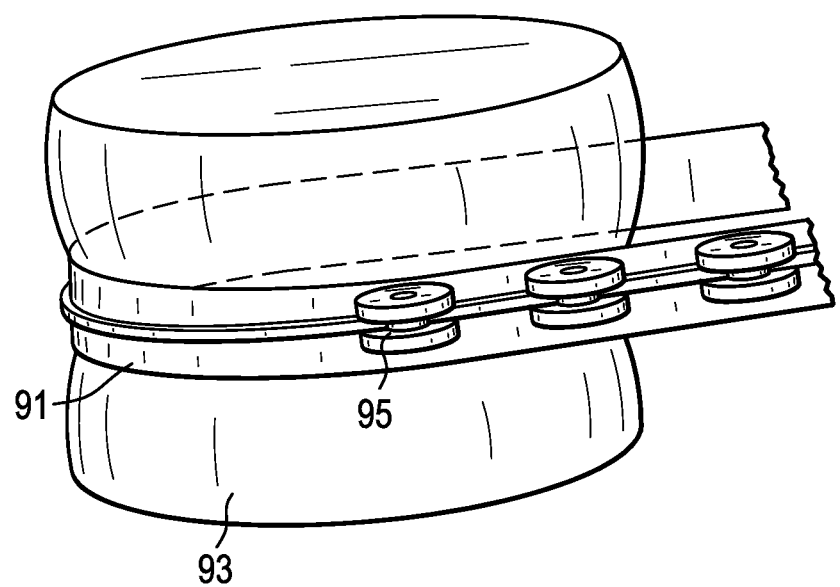
FIG. 10 illustrates an inflated balloon having magnetic wheels on its track.

FIG. 10 discloses an embodiment showing means for transporting instruments along a track 91 on the central inflatable balloon 93. A plurality of magnetic wheels 95 are shown travelling along a track. These wheels can be used to transport instruments into and from the disc space.

Figure 11A:
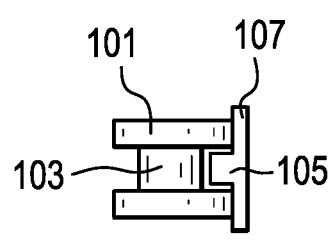
FIGS. 11A-11B depicts cross-sections of magnetic-wheel/track engagement.

FIG. 11A shows details of how the magnetic wheel 101 can be attached to the track. The wheel has a central magnet 103 that contacts central rail 105 of the track 107. The overlap keeps the instrument in line.

Figure 11B:
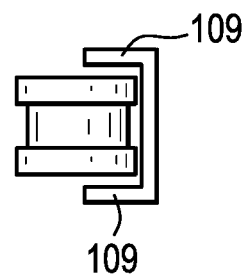

FIG. 11B shows another embodiment of the wheel-track engagement, wherein the track has a pair of side rails 109 that keep the wheel engaged.

FIG. 12 shows a pair of docking ports 111 bilaterally disposed on a central inflatable balloon 113. An instrument 115 can have a distal docking ball 117 for reception by the docking port. In this case, the instrument has an articulating scraper 119 attached thereto for scraping tissue in the disc space.

Figure 13:
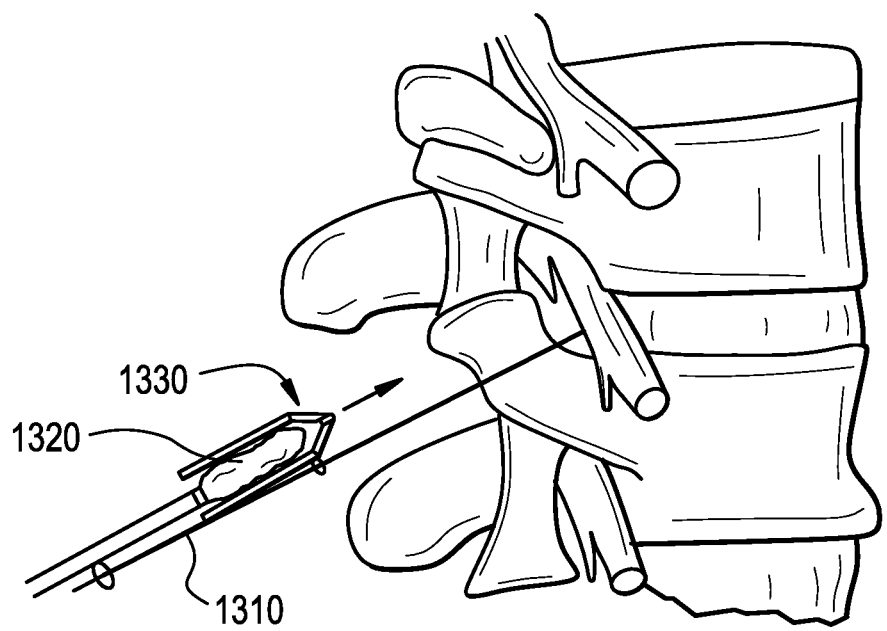
FIG. 13 depicts a method of introducing distraction and fusion devices into a disc space without using a cannula.

FIG. 13 discloses a method of introducing the distraction and fusion devices in an over-the-wire method. A guidewire 1310 directs the distraction and fusion devices into the disc space, thereby avoiding the risk of damaging nerves or other fragile anatomy. Connection points are embedded on the distraction and fusion device assemblies keep the devices in line with the guidewire as they pass through the body into the disc space. In some embodiments, a protective cover 1330 prevents damage to the inflation devices 1320 during passage through body tissues, the disc annulus, and collapsed endplates.

Figure 14A:
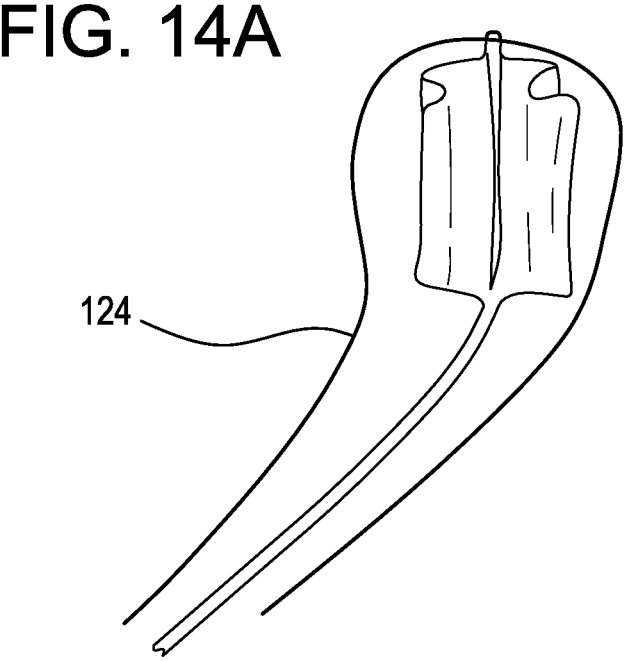
FIGS. 14A, B and C show a method of introducing perimeter and central balloons into a disc space.
Figure 14B:
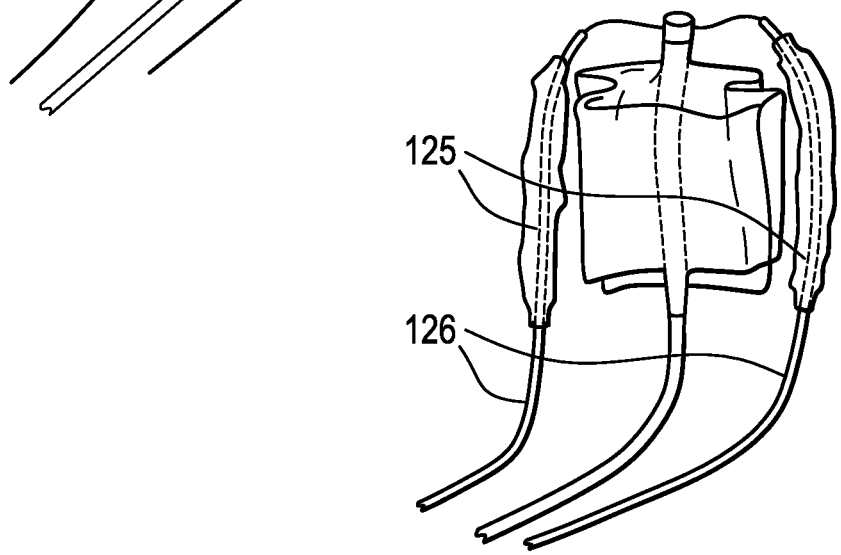
Figure 14C:
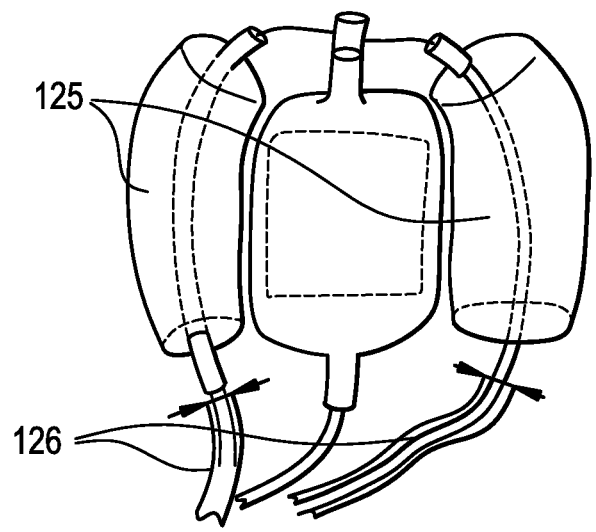

FIGS. 14A-14C disclose a process for introducing the central and perimeter balloons accurately into the correct disc space location while each balloon travels into the disc space independently, thereby allowing larger inflation devices, a smaller pathway through the body, or a combination of the two. Guidewires 124 are attached and inserted with the central inflation device. Perimeter balloons 125 slide on the guidewire into the correct position surrounding the central balloon, creating a dual perimeter balloon system that is generally annular in shape. The perimeter balloon inflation lumens 126 run from the perimeter balloons to the inflation point outside of the patient body. A double set of concentric lumens allows the guidewire to pass through and the balloon to be inflated. The lumens may be removed after the perimeter balloons are hardened.

Figure 16A:
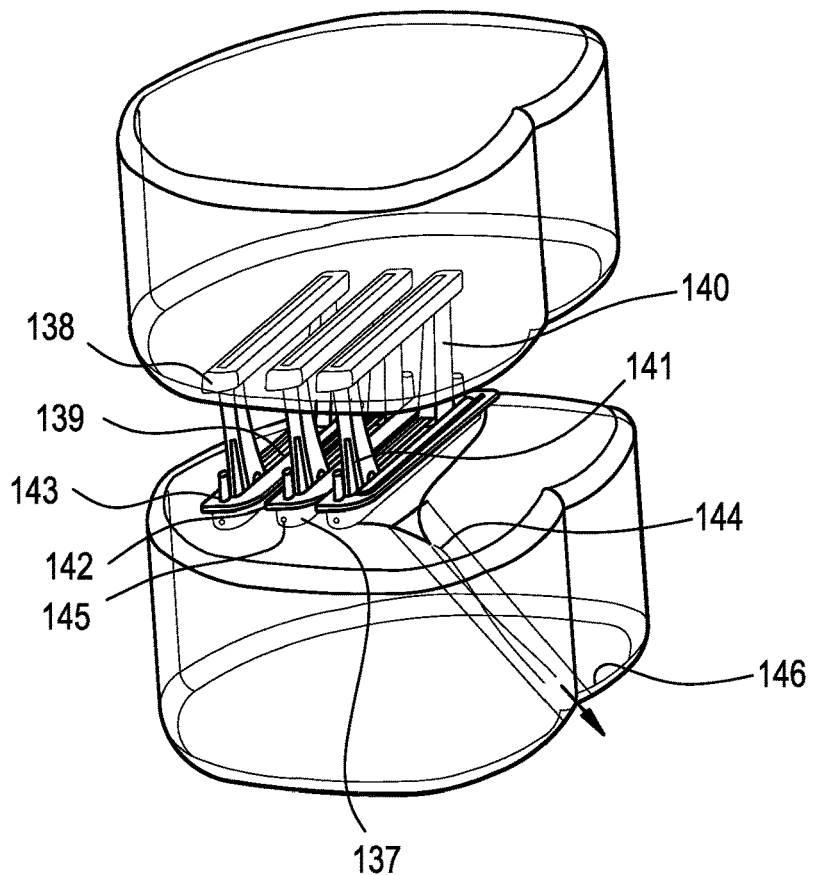
FIG. 16A illustrates a cam assembly that may be used as a distraction device in accordance with an embodiment of the invention.
Figure 16B:
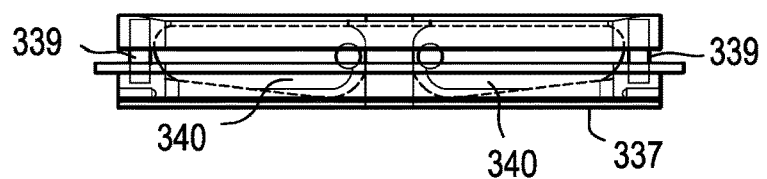
FIG. 16B shows a cam of FIG. 16A in a collapsed configuration.
Figure 16C:
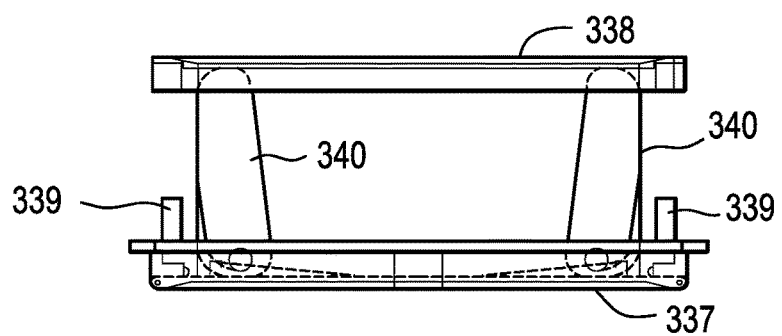
FIG. 16C depicts the cam of FIG. 16A fully rotated.
Figure 16D:
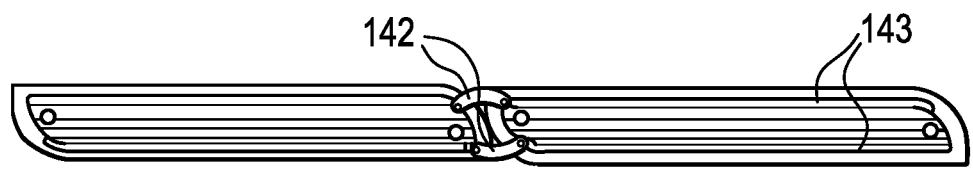
FIGS. 16D-16F illustrate sliders of the cam assembly shown in FIG. 16A.
Figure 16E:
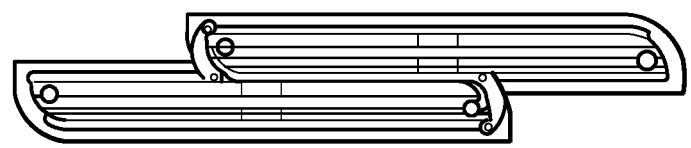
Figure 16F:
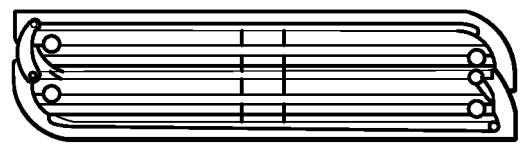

FIG. 16A discloses an alternate embodiment of a distraction device in accordance with the invention which utilizes one or more cam assemblies to distract the vertebral body. Each cam assembly may comprise first and second cams 140 where each cam 140 has a lower end slidably engaged with lower track 137 and an upper end engaging upper track 138. As shown in FIG. 16B, cams 140 are disposed substantially parallel to the major axis of tracks 137 and 138 during insertion into the disc space. The slim aspect ratio of the cams 140 facilitates insertion in a minimally invasive manner into the disc space. Once inserted, one or multiple cam assemblies can be positioned as desired and then rotated via an actuation means or expansion means, such as pull lines 144, gears, rotating shaft, or belt, to provide lift as illustrated in FIG. 16C. In the FIG. 16A, pull lines 144 are routed through holes 145 in the lower track 137 and directed through the access point with a cannula 146. The cannula may be used to provide the reaction force needed to keep tracks 137 in place as the pull lines are pulled. The rotation of cams 140 may be controlled using upper grooved track 138 and lower grooved track 137. The tracks 137 and 138 also distribute the distraction load from cams 140 over a large surface, thereby decreasing the risk of damage to the vertebral endplates. An additional set of mating grooves 141 and rails (not shown) may be provided in the middle of each cam 140 and lower track 137 to further control alignment. Where the cam assembly includes multiple lower tracks 137, they may link together using a rigid linkage 142 that slides along a slot 143 which may be disposed along an edge of lower track 137 as illustrated in FIG. 16D. This allows multiple lower tracks 137 to be inserted minimally invasively in a line, end-to-end, and then rotated to sit with their long sides touching as illustrated in FIGS. 16E, and 16F. The collapsed track/cam assembly may be secured together during insertion using pins 139.

In some embodiments, one or more cam assemblies may be used in the central space of a perimeter balloon and may either remain permanently in the disc space or be removed after the perimeter balloon is hardened. In other embodiments, the cam assemblies may be positioned around the perimeter of the disc space and provide the distraction either by themselves or in conjunction with a central distraction balloon. In still other embodiments, cam assemblies may be spaced through the disc space and are used without any other distraction devices.

Figure 17:
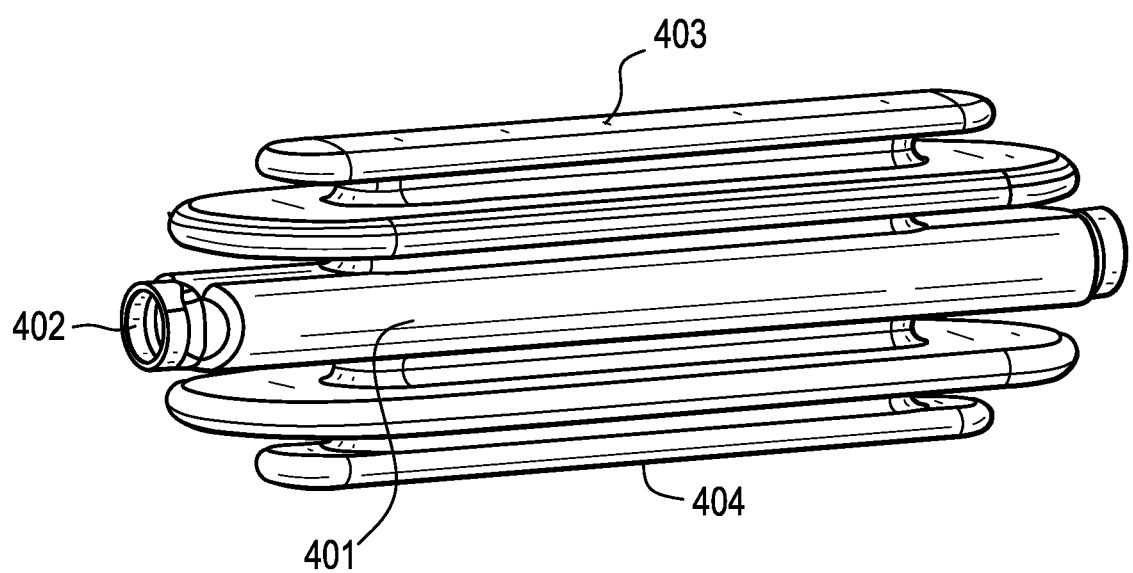
FIG. 17 illustrates a bellows assembly that may be used as a distraction device in accordance with an embodiment of the invention.

FIG. 17 discloses still another embodiment a distraction device which utilizes one or more metallic bellows to distract the vertebral unit. A bellow body or chamber 401 is made of a thin-walled metal, such as titanium comprising a plurality of pleats. As pneumatic fluid, hydraulic fluid, or small discrete masses of solid material (such as beads) are inserted under pressure into the inlet 402 of the bellow, the metal expands vertically and applies distraction force to the vertebral endplates. The distraction force is transmitted to the superior vertebral endplate along bellow upper surface 403 and is transmitted to the inferior vertebral endplate along bellow lower surface 404. The metal may plastically deform as it expands thereby resisting collapse to its original compressed shape. The space around the bellow(s) will be packed with bone graft and the expanded bellow(s) will be provide the support structure while the bony fusion forms. The bellow may provide the support via the plastically deformed structure, fluid pressure inside the bellow structure, a hardened material inside the bellow structure, or some combination of these. Multiple bellows may be used to distribute lift forces on the vertebral endplates and/or to increase the distraction force applied. The bellows may be inserted minimally invasively by making use of the thin aspect ratio of one of its sides. In some embodiments, the walls of the bellows contain pores that, when the device is inflated with an osteogenic material or matrix, allows for fusion to the endplates through the device.

In some embodiments, one or more bellows may be used in the central space of a perimeter balloon and may either remain permanently in the disc space or be removed after the perimeter balloon is hardened. In other embodiments, the bellows may be positioned around the perimeter of the disc space and provide the distraction either by themselves or in conjunction with a central distraction balloon. In still other embodiments, bellows may be spaced through the disc space and used without any other distraction devices.

Figure 18A:
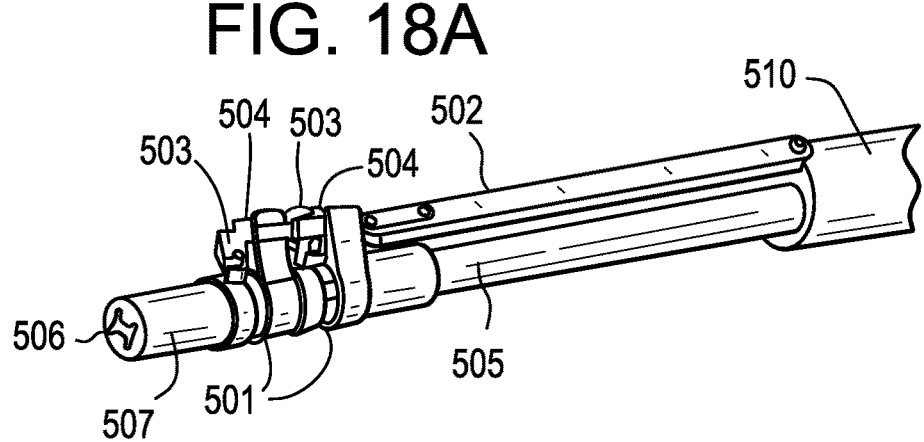
FIGS. 18A-C show a spooling device that may be used as a distraction device in accordance with an embodiment of the invention.
Figure 18B:
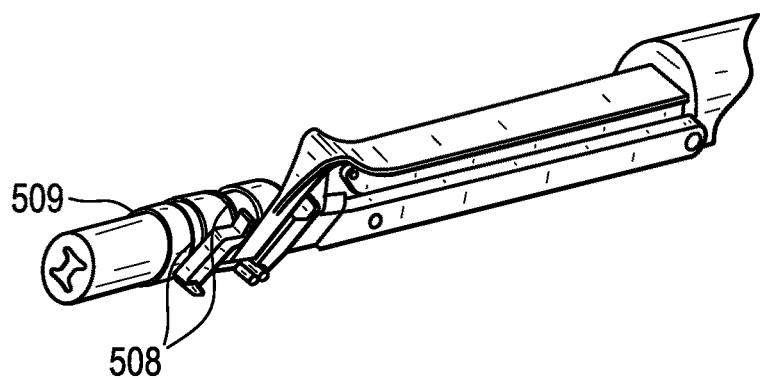
Figure 18C:
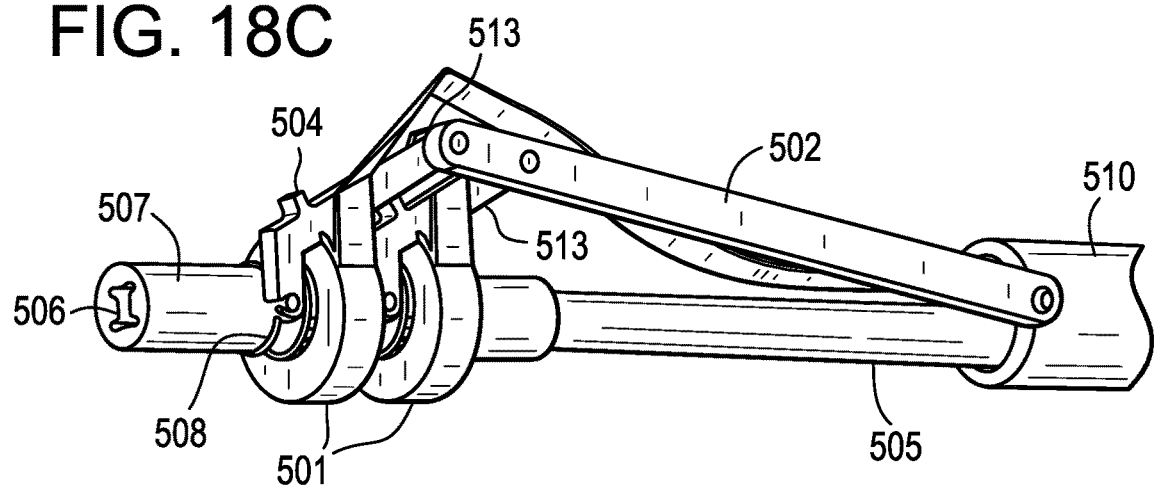
Figure 18D:
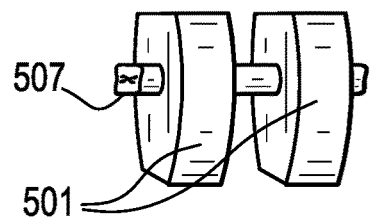
FIG. 18D depicts spooled ribbon disposed between vertebral endplates.

FIG. 18A-18C disclose yet another embodiment of the distraction device which utilizes a spooling mechanism of a long, thin ribbon to distract the vertebral body. The spooling mechanism includes one or more ribbons 501 be fed through a stationary base 510 at a proximal end. Ribbons 501 may be made of polymeric material or metal and, in some embodiments, they are predominantly flexible in one axis due to their thinness. Each ribbon 501 is routed along a linkage arm 502 which itself is pivotably coupled to stationary base 510 at its proximal end and to a guide linkage 503 at its distal end. Guide linkage 503 includes first and second guide arms 513 each including a guidepost 504 which extends generally orthogonally from respective guide arms 513. The ribbon is pulled in tension towards the base 510; as the ribbon passes over guideposts 504, the ribbon is redirected perpendicular to the reel 507; ribbon tension is maintained and the ribbon is spooled onto the reel in a controlled manner. A rotor 505 extends from base 510 through ribbon reel 507 and is driven by a drive mechanism (not shown) and drives a ribbon reel 507. In some embodiments rotor 505 engages ribbon reel 507 through a mechanical linkage, e.g., by, a tongue and groove connection or ball and socket type linkage. In the embodiment illustrated in FIGS. 18A-18C, rotor 505 engages ribbon reel 507 by means of a geometry on rotor 505's distal end that mates with a geometry 506 on the distal end of ribbon reel 507 Guide linkage 503 is connected to ribbon reel 507 via bearings 508 with pin joints 518. The bearings 508 are positioned on ribbon reel 507 with retaining rings 509 but allowed to rotate freely along the long axis of ribbon reel The device may be inserted with minimal invasiveness because the linkage arm 502, guide linkage 503 and ribbons 501 can collapse down along rotor 505; when in the interbody space as shown in FIGS. 18A and 18B. The stationary base 510 may be advanced distally causing linkage arm 502 and guide linkage 503 to rotate at the pin joints 518 and create distance between themselves and rotor 505 as in FIG. 18C. Rotor 505 then is driven from the proximal end, which causes the ribbon(s) 501 to spool on the reel. The distraction distance may be controlled by the amount of ribbon spooled and/or the thickness of each ribbon material. The one or more ribbons 501 are then cut at the guide linkage 503 and the base 510, rotor 505, guide linkage 503 and linkage arm 502 are retracted, leaving the spooled ribbons 501 and ribbon reel 507 in the interbody space, providing the support structure for a bony fusion. In some embodiments, the cavity left through the middle of the reel when the rotor is retracted will collapse in the absence of the rotor and create a flatter upper and lower surface for the spooled ribbon, thereby making a larger contract area between the ribbon and the vertebral end plates such as depicted in FIG. 18D. Bone graft is then packed into the remaining cavity of the interbody space.

Although shown and described in what is believed to be the most practical embodiments, it is apparent that departures from specific designs and methods described and shown will suggest themselves to those skilled in the art and may be used without departing from the spirit and scope of the invention. For example, the curable material of any of the disclosed embodiments may be radiopaque and/or include Tantalum marker beads to facilitate registration on fluoro scans. The perimeter balloon or the central balloon may also be provided with markers.

The present invention is not restricted to the particular constructions described and illustrated, but should be construed to cohere with all modifications that may fall within the scope of the appended claims.

What is claimed is:

1. An apparatus for forming an intervertebral fusion device comprising:
   a central distraction device including a first lumen, the first lumen having a distal end portion and a proximal end portion and including an inflatable distractor attached to the distal end portion;
   a perimeter distraction device including a second lumen, the second lumen having a distal end portion and a proximal end portion, and including an inflatable balloon attached to the distal end portion;
   a coupling device configured to couple the proximal end of the first lumen to the proximal end of the second lumen; and
   first and second connection members disposed at respective proximal end portions of the first and second lumens, wherein said first and second connection members are configured to couple with said coupling device.

2. The apparatus of claim 1 further comprising an inflation controller connected to the first and second lumens.

3. The instrument of claim 1 further comprising a locking arm configured to connect to one of the first and second connection members at a proximal end and to a rigid surface at a distal end.

4. The instrument of claim 3 wherein said locking arm is articulated.

5. An apparatus for forming an intervertebral fusion device comprising:
   first and second guidewires;
   a central distraction device attached to said first and second guidewires;
   a first perimeter balloon assembly including a first perimeter balloon having first concentric guidewire and inflation lumens, the first guidewire lumen extending through an inner diameter of said first perimeter balloon and the first inflation lumen extending from the first perimeter balloon to an external inflation point; and
   a second perimeter balloon assembly including a second perimeter balloon having second concentric guidewire and inflation lumens, the second guidewire lumen extending through an inner diameter of said second perimeter balloon and the second inflation lumen extending from the second perimeter balloon to an external inflation point;
   said first guidewire extending through the guidewire lumen of said first perimeter balloon and said second guidewire extending through the guidewire lumen of said second perimeter balloon.

6. The apparatus of claim 5 further comprising an inflation controller connected to the first and second inflation lumens.

* * * * *